United States Patent
Carell

(10) Patent No.: US 9,480,752 B2
(45) Date of Patent: Nov. 1, 2016

(54) ANANDAMIDE-MODIFIED NUCLEIC ACID MOLECULES

(71) Applicant: BASECLICK GMBH, Tutzing (DE)

(72) Inventor: Thomas Carell, Krailling (DE)

(73) Assignee: Baseclick GmbH, Tutzing (DE)

( * ) Notice: Subject to any disclaimer, the term of this patent is extended or adjusted under 35 U.S.C. 154(b) by 0 days.

(21) Appl. No.: 14/413,926

(22) PCT Filed: Jul. 10, 2013

(86) PCT No.: PCT/EP2013/064610
§ 371 (c)(1),
(2) Date: Jan. 9, 2015

(87) PCT Pub. No.: WO2014/009429
PCT Pub. Date: Jan. 16, 2014

(65) Prior Publication Data
US 2015/0209441 A1     Jul. 30, 2015

(30) Foreign Application Priority Data
Jul. 10, 2012   (EP) .................................... 12175737

(51) Int. Cl.
| | |
|---|---|
| *C07H 21/02* | (2006.01) |
| *C07H 21/04* | (2006.01) |
| *A61K 47/48* | (2006.01) |
| *A61K 31/713* | (2006.01) |
| *C12N 15/113* | (2010.01) |
| *C07H 19/16* | (2006.01) |
| *C07H 19/04* | (2006.01) |
| *C07H 19/06* | (2006.01) |

(52) U.S. Cl.
CPC ....... *A61K 47/48038* (2013.01); *A61K 31/713* (2013.01); *C12N 15/113* (2013.01); *C07H 19/04* (2013.01); *C07H 19/06* (2013.01); *C07H 19/16* (2013.01); *C12N 2310/14* (2013.01); *C12N 2310/351* (2013.01); *C12N 2320/32* (2013.01)

(58) Field of Classification Search
None
See application file for complete search history.

(56) References Cited

U.S. PATENT DOCUMENTS

2002/0025943 A1*   2/2002   Bradley ................. C07H 19/06
                                                                      514/49

FOREIGN PATENT DOCUMENTS

| EP | 2 264 167 A1 | 12/2010 |
|---|---|---|
| WO | 2004/065601 A2 | 8/2004 |
| WO | 2009/126933 A2 | 10/2009 |

OTHER PUBLICATIONS

Yamada et al. J. Org. Chem. (2011), vol. 76, pp. 1198-1211.*
Akinc, Akin et al., "A Combinatorial Library of Lipid-Like Materials for Delivery of RNAi Therapeutics", Nature Biotechnology, vol. 26, No. 5 (May 2008), pp. 561-569.
Paredes, Eduardo et al., "Click Chemistry for Rapid Labeling and Ligation of RNA", ChemBioChem vol. 12 (2011), pp. 125-131.
Wolfrum, Christian et al., "Mechanisms and Optimization of in vivo Delivery of Lipophilic siRNAs", Nature Biotechnology, vol. 25, No. 10 (Oct. 2007), pp. 1149-1157.
International Search Report for PCT/EP2013/064610, dated Oct. 7, 2013.

* cited by examiner

*Primary Examiner* — Patrick Lewis
(74) *Attorney, Agent, or Firm* — Brinks Gilson & Lione

(57) ABSTRACT

The present invention refers to a conjugate comprising at least one polyunsaturated fatty acid residue, particularly an arachidonic acid residue, more particularly an anandamide (arachidonoyl ethanol amide) residue and covalently bound thereto at least one nucleosidic component selected from nucleic acids, nucleosides and nucleotides. This conjugate is suitable for the transfection of cells such as mammalian cells including human cells with high efficacy. Thus, a new delivery vehicle for therapeutic molecules including antisense molecules, siRNA molecules, miRNA molecules, antagomirs or precursors of such molecules, as well as the therapeutic nucleosides or nucleotides, is provided.

18 Claims, 23 Drawing Sheets

Figure 1:
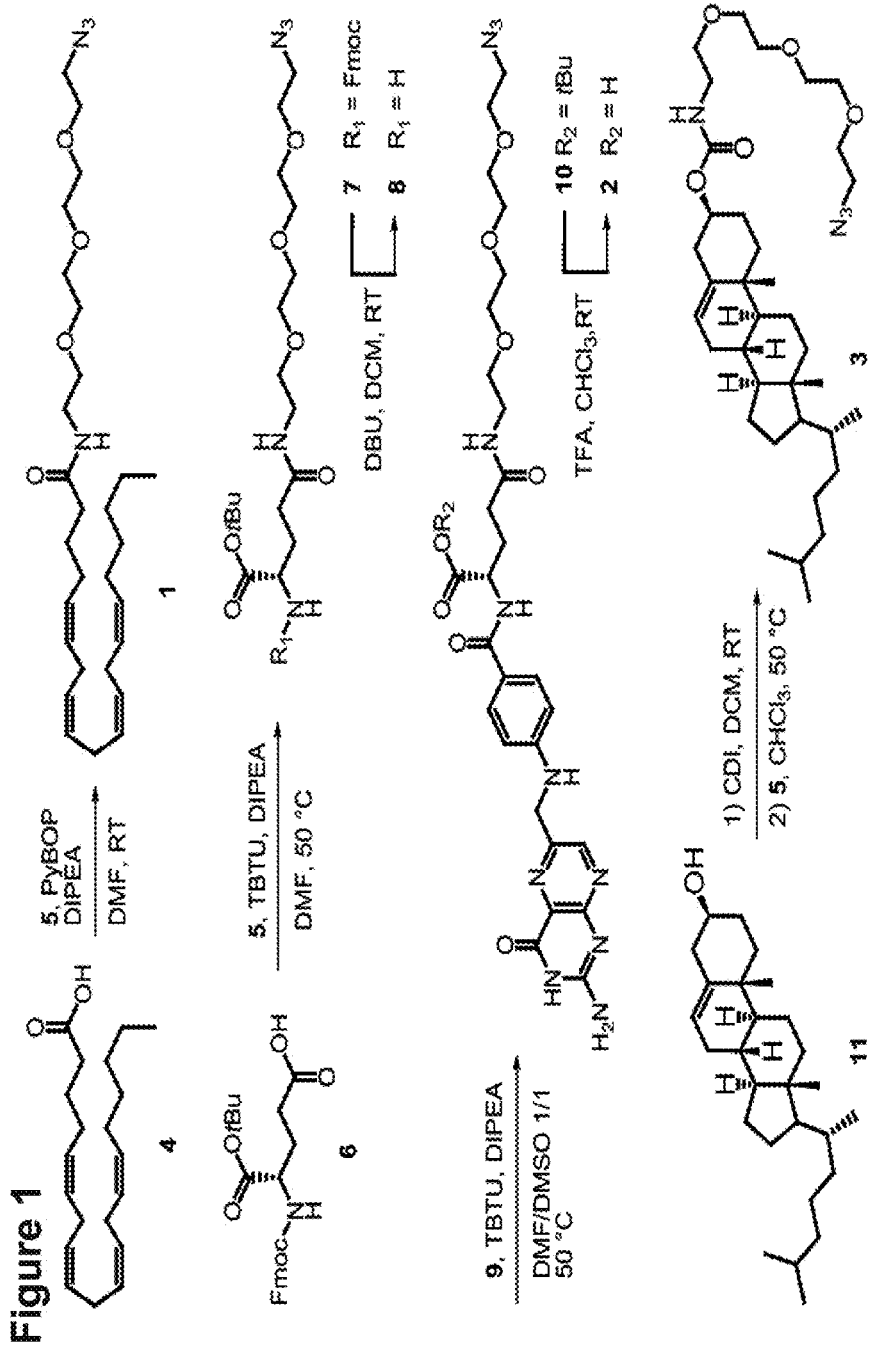

Synthesis of a nine fold azide-modified anandamide

Covalent anandamide-modification of RNA-oligonucleotides via CuAAC

1. Modification of the two senses strands with the nine-azide

1. Modification of the two senses strands with the nine-azide

1. Influence of the siRNAnumber per Anandamide

ANANDAMIDE-MODIFIED NUCLEIC ACID MOLECULES

This application is a National Stage application of International Application No. PCT/EP2013/064610 filed Jul. 10, 2013, the entire contents of which is hereby incorporated herein by reference. This application also claims priority under 35 U.S.C. §119 to European Patent Application No. 12175737.1 filed Jul. 10, 2012, the entire contents of which is hereby incorporated herein by reference.

The present invention refers to a conjugate comprising at least one polyunsaturated fatty acid residue, particularly an arachidonic acid residue, more particularly an anandamide (arachidonoyl ethanol amide) residue and covalently bound thereto at least one nucleosidic component selected from nucleic acids, nucleosides and nucleotides. This conjugate is suitable for the transfection of cells such as mammalian cells including human cells with high efficacy. Thus, a new delivery vehicle for therapeutic molecules including antisense molecules, siRNA molecules, miRNA molecules, antagomirs or precursors of such molecules, as well as the therapeutic nucleosides or nucleotides, is provided.

RNA interference is a powerful tool that utilizes short RNA double strands to repress the formation of a particular protein in a cell (1-3). In nature, the silencing RNA molecules are produced from larger transcripts that are cut by the Dicer complex (4). For biotechnological application, however, the RNA molecules (siRNA) are chemically prepared and administered. The idea to use siRNA as therapeutic agents (5), was intensively pursued in the last decade but the major obstacle, the poor cellular uptake of RNA duplexes, could not be overcome (6) Currently, RNA delivery systems as divergent as nanoparticles (7,8), liposomes (9,10), or polycation polymers (11) are under intensive investigation. Despite substantial progress in the field, however, the often still high toxicity (12-14) and low cellular specificity represent problems that are not solved.

Most recently, receptor mediated endocytosis has evolved as an alternative delivery strategy (16-25) that allows targeting of the siRNA to special cell types. The method requires linking the siRNA to a ligand that binds to a cell type specific receptor. This initiates an internalization process leading to the uptake of the RNA-ligand conjugate. Currently, the strategy is most successfully implemented with cholesterol modified RNA (24).

Here, we report that such a receptor mediated strategy can be successfully used to solve the problem that sensitive cells such as neuronal cells (26,27) and immune cells (28) are up to now difficult to transfect. We discovered, that the cannabinoid receptor present on both cell types (29), can be efficiently targeted with an arachidonoyl ethanol amide (30,31) (anandamide) modified siRNA.

A first aspect of the present invention is a conjugate comprising a polyunsaturated fatty acid residue and covalently bound thereto at least one nucleosidic component selected from nucleic acids, nucleosides and nucleotides.

The term "conjugate" also encompasses salts, particularly pharmaceutically acceptable salts, e.g. addition salts with inorganic or organic acids or bases as known in the art.

The conjugate comprises at least one polyunsaturated fatty acid residue, particularly 1-10, more particularly 1-5 fatty acids. Even more particularly, the conjugate comprises 1 or 2 polyunsaturated fatty acid residues. Most particularly, the conjugate comprises 1 polyunsaturated fatty acid residue.

In a particular embodiment, the polyunsaturated fatty acid residue is an arachidonic acid (AA) residue, more particularly an arachidonoyl ethanol amide (anandamide) acid residue.

In a further particular embodiment, the nucleosidic component attached to the polyunsaturated fatty acid residue is a nucleic acid molecule, more particularly an RNA molecule.

The conjugate comprises at least one nucleosidic component, particularly 1-25, more particularly 2-20 or 2-10, and even more particularly 2-8, i. e. 2, 3, 4, 5, 6, 7 or 8 nucleosidic components. If the conjugate comprises more than one nucleosidic component, the nucleosidic components may be identical or different.

In a further particular embodiment, the conjugate comprises 1 polyunsaturated fatty acid residue such as an anandamide residue and 2-20, particularly 2-8, i.e. 2, 3, 4, 5, 6, 7 or 8 nucleosidic components.

In one embodiment, the conjugate may have a linear structure. Thus, nucleosidic components can be connected in a linear chain, wherein a polyunsaturated fatty acid residue may be present within the chain, at one end of the chain or at both ends of the chain.

In another embodiment, the conjugate has a branched structure, wherein nucleosidic components are bound to an polyunsaturated fatty acid residue via a branched linker, e.g. a dendrimeric linker.

The term "polyunsaturated fatty acid residue" includes a free fatty acid residue, but also a fatty acid derivative residue, particularly a fatty acid ester residue, or a fatty acid amide residue, a fatty acid sulfonate residue, a fatty acid sulfate residue, a fatty acid phosphonate residue, a fatty acid phosphate residue etc. The polyunsaturated fatty acid residue is provided with a functional group to which the at least one nucleosidic component may be covalently bound. The functional group may be the carboxy group of the fatty acid or another functional group, e.g. a functional group present on the alcohol of an ester residue or a functional group present on the amine of an amide residue, which may e.g. be an OH or an $NH_2$ group. The alcohol moiety of an ester residue may e.g. be a $C_{1-5}$ alcohol which has an additional functional group, e.g. ethylene glycol, propylene glycol, or glycerol. The amine moiety of an amide residue may be a $C_{1-5}$ amine which has an additional functional group, e.g. ethanol amine, propanol amine or ethylene diamine.

The polysaturated fatty acid residue present in the conjugate is preferably a polyunsaturated $C_{16}$-$C_{24}$ fatty acid residue, particularly a $C_{18}$, $C_{19}$, $C_{20}$, $C_{21}$ or $C_{22}$ fatty acid residue, more particularly a $C_{20}$ fatty acid residue. The polyunsaturated fatty acid residue has at least 2 C=C bonds, particularly 3, 4, 5 or 6 and more particularly 4 C=C bonds. At least 1-5, particularly 4 C=C bonds are in the Z-configuration. More particularly all double bonds are in the Z-configuration.

Specific examples of polyunsaturated fatty acid residues are selected from from a cis-5, 8, 11, 14-eicosatetraenoic acid (arachidonic acid) residue, a cis-5, 8, 11, 14, 17-eicosapentaenoic acid (EPA) residue, a cis-4, 7, 10, 13, 16, 19-docosahexaeonoic acid (DHA) residue, a cis-6, 9, 12-octadecatrienoic acid (GLA) residue, and a cis-8, 11, 14-eicosatrienoic acid (DGLA) residue. More particularly, the fatty acid residue is an arachidonic acid residue. In an especially preferred embodiment, the fatty acid residue is an arachidonoyl ethanol amide (anandamide).

The fatty acid residue is covalently bound to at least one nucleosidic component Preferably, the fatty acid residue is bound to the at least one nucleosidic component via a linker.

The linker may be a linear or a branched linker and usually has a chain length of from 2-50 atoms, including carbon atoms and particularly heteroatoms such as S, N, and/or O-atoms.

For example, the linker may be a linear linker, e.g. a linker comprising at least one, e.g. from 1-10, particularly from 2-5 and more particularly 3 $C_1$-$C_3$ alkylene oxide groups, particularly ethylene oxide groups.

Alternatively, the linker may be a branched, e.g. dendrimeric linker.

The polyunsaturated fatty acid residue may be connected to the at least one nucleosidic component via known linker techniques. Preferably however, the attachment involves a Click reaction, e.g. between an azide and an alkyne group, between a constrained alkene, e.g. a norbornene and a nitrile irmine, a nitrile oxide, or a tetrazine, thereby resulting in a cyclic group formed by the Click reaction, particularly a 1,2,3-triazole group.

In a preferred embodiment, the polyunsaturated fatty acid residue is a receptor ligand, preferably a ligand of a receptor present in the membrane of a eukaryotic cell, particularly a receptor present in the membrane of a mammalian cell, e.g. a human cell. More preferably, the polyunsaturated fatty acid residue is a ligand of a cannabinoid receptor as described (48), the content of which is incorporated herein.

In a particular embodiment, the conjugate of the present invention is represented by the general Formula (Ia) or (Ib)

$$F_n\text{-}(L_m\text{-}N)_r \quad (Ia)$$

$$F_n\text{-}(L_m\text{-}N)_r\text{-}L_m\text{-}F_n \quad (Ib)$$

wherein
F is a polyunsaturated fatty acid residue,
L is a linker,
N is a nucleosidic component selected from nucleis acids, nucleosides and nucleotides,
n is an integer from 1-10, preferably from 1-5, more preferably 1,
m is 0 or 1,
r is an integer from 1-25,
preferably from 2-20 and
more preferably from 2-8.

In this embodiment, the conjugate may be represented by structures such as:

F-L-N

F-(L-N)$_r$ wherein F, L, N and r are as defined above,

F-L*-(N)$_r$ wherein L* is a branched linker and F, N and r are as defined above, F-(L-N)$_r$-L-F wherein F, L, N are r are as defined above.

In another embodiment, the conjugate may comprise a further receptor ligand, covalently bound to the at least one nucleosidic component. The further receptor ligand is a compound different from a polyunsaturated fatty acid residue such as folate, cholesterol, or a hormone.

In this embodiment, the conjugates may be represented by a structure having the general Formula (II)

$$F_n\text{-}(L_m\text{-}N)_r\text{-}L_m\text{-}Z_s \quad (II)$$

wherein
F is a polyunsaturated fatty acid residue,
L is a linker,
n is an integer from 1-10, preferably from 1-5, more preferably 1,
m is 0 or 1,
N is a nucleosidic component selected from nucleic acids, nucleosides and nucleotides,
r is an integer from 1-25,
preferably from 2-20 and
more preferably from 2-8,
Z is a further receptor ligand, and
s is an integer from 1-10, preferably from 1-5, more preferably 1.

In this embodiment, the conjugate may be represented by structures such as:

F-L-N—Z

F-(L-N)$_r$-L-Z wherein F, L, N, A and r are as defined above,

F-L*-(N)$_r$-L-Z

L* is a branched linker and F, L, N, Z and r are as defined above,

The conjugate of the present invention comprises at least one nucleosidic component selected from nucleic acids, nucleosides and nucleotides.

The term "nucleic acid" encompasses single-stranded and double-stranded nucleic acid molecules, e.g. DNA molecules or RNA molecules and analogues thereof. An analogue of a nucleic acid is a nucleic acid molecule which comprises at least one modified building block as described below.

In one embodiment, the nucleic acid molecule is a DNA molecule which may comprise at least one modified building block. The term "DNA molecule" encompasses single-stranded or double-stranded DNA molecules. In double-stranded DNA molecules, the individual strands may be present in separate molecules or being covalently connected via a single-stranded loop or via heterologous linker.

The term "DNA molecule" encompasses molecules consisting of natural DNA building blocks, i.e. 2'-deoxyribonucleotide building blocks, and molecules comprising at least one modified building block.

In a further embodiment, the nucleic acid molecule is an RNA molecule, which may comprise at least one modified building block. The term "RNA molecule" encompasses single-stranded or double-stranded RNA molecules, wherein double-stranded RNA molecules may have at least one overhang, e.g. at least one 3'-overhang. In double-stranded RNA molecules, the individual strands may be present as separate molecules or being covalently connected via a single-stranded loop or via a heterologous linker.

The term "RNA molecule" encompasses molecules consisting of natural RNA building blocks, i.e. 2'-ribonucleotide building blocks, and molecules comprising at least one modified building block.

Modified building blocks may be selected from sugar-, backbone- and/or nucleobase-modified building blocks. Sugar-modified deoxyribonucleotides comprise a sugar group different from deoxyribose, e.g. a modified deoxyribose group, wherein the 2'-H group is replaced by a group selected from OH, R, OR, halo, SH, SR, $NH_2$, $NHR$, $NR_2$ or CN, wherein R is $C_1$-$C_6$ alkyl or alkoxy, or $C_2$-$C_6$ alkenyl or alkynyl and halo is F, Cl, Br, I. Specific examples of 2'-H modifications are 2'-F and 2'-O methyl. Sugar-modified ribonucleotides comprise a sugar group different from ribose, e.g. a modified ribose group, wherein the 2'-OH group is replaced by a group selected from H, R, OR, halo, SH, SR, NH$_2$, NHR, NR$_2$ or CN, wherein R is C$_1$-C$_6$ alkyl or alkoxy, or C$_2$-C$_6$ alkenyl or alkynyl and halo is F, Cl, Br, I. Specific examples of 2'-OH modifications are 2'-F and 2'-O methyl. In a backbone-modified building block, the phosphoester group connecting adjacent building blocks may be replaced by a modified connecting group, e.g. a phosphorothioate group. In nucleobase-modified building blocks, a non-naturally occurring nucleobase may be present instead of a naturally occurring nucleobase. Corresponding analogues of purine or pyrimidine nucleobases are well known in the art. It should be noted that the above modifications may be combined.

The nucleic acid molecule is preferably selected from nucleic acid molecules which are suitable for pharmaceutical applications, particularly from antisense molecules, or from RNA molecules capable of mediating RNA interference such as siRNA molecules or precursors thereof. Further suitable RNA molecules include miRNA molecules, antagomirs, ribozymes and precursors thereof.

The term "nucleosidic component" also encompasses nucleosides or nucleotides and analogues thereof. A nucleoside is a compound comprising a nucleobase and a sugar group. A nucleotide compound is a compound comprising a nucleobase, a sugar group and a phosphate group. Sugar-, phosphate- and nucleobase-modified compounds are also encompassed by the present invention, particularly nucleoside or nucleotide analogue therapeutics which are suitable for the treatment of cancer and/or viral infections, such as AZT, aciclovir, ganciclovir, valaciclovir, gemcitabine, cytarabine, etc.

The nucleosidic component may be connected to the fatty acid residue via a nucleobase, a sugar, or a phosphate group of the molecule. If the compound is a nucleic acid, it may be connected via a building block present in the nucleic acid molecule, particularly via a terminal building block, i.e. a building block located at the 5' or 3'-terminus of a nucleic acid strand, more particularly via a 3'-terminal building block of a nucleic acid strand. In a preferred embodiment, the connection occurs via a modified terminal nucleobase present in a nucleic acid molecule, particularly in an RNA molecule.

In a preferred embodiment, the covalent linkage to the polyunsaturated fatty acid residue may be attached to a nucleobase present in the nucleosidic component, e.g. of a building block of a DNA or RNA molecule, e.g. to position 8 of a purine base or to position 5 of a pyrimidine base.

A nucleic acid molecule, e.g. a DNA or RNA molecule, usually has a length of from 5, 10, 12, 15 or 18 building blocks and up to 25, 30, 50 or 100 building blocks or more. The nucleic acid molecule may be prepared by chemical synthesis or by enzymatic methods from nucleic acid templates, e.g. by transcription, catalysed by an RNA polymerase, e.g. by T3, T7 or SP6 RNA polymerase, or by DNA replication or by reverse transcription. Preferably, during chemical or enzymatic synthesis, a building block is incorporated comprising a functional group, e.g. a Click-functional group, e.g. a terminal alkyne group, or an azide group, a constrained alkene group, such as a norbornene group, a nitrile oxide group, a nitrile imine group or a tetrazine group. In a particular embodiment, a building block which is modified by including a terminal alkyne group, optionally via a linker, is incorporated. Methods of introducing Click-modified building blocks into nucleic acid molecules are described in WO2006/117161 and WO2008/052775, the contents of which are herein incorporated by reference. The functional group on the nucleosidic component may be coupled to a complementary functional group which is attached to the polyunsaturated fatty acid residue according to known methods. Preferably, the coupling is carried out by e.g. a Click-reaction with a complementary Click-functional reactive group, e.g. an azide group.

Alternatively, a modified nucleic acid building block linked to the polyunsaturated fatty acid residue may be introduced into a nucleic acid, e.g. an RNA molecule, during a solid phase synthesis according to standard methods, e.g. using a phosphoramidite building block.

The present invention also provides a reagent for manufacturing a conjugate of the invention having the general formula (V)

$$F_n\text{-}(L')_m\text{-}(RG1)_r \quad\quad\quad (V)$$

wherein

F, n, m and r are as defined above,

L' is a linker, and

RG1 is a reactive group, particularly a Click-reactive group such as an azide group.

A further reagent for manufacturing a nucleic acid conjugate of the invention, having the general formula (VI), is also provided:

$$BB\text{-}(L)_m\text{-}F_n \quad\quad\quad (VI)$$

wherein

F, L, n and m are as defined above, and

BB is a building block for synthesizing a nucleic acid molecule, e.g. a nucleoside triphosphate, or a building block suitable for solid phase synthesis, e.g. a phosphoramidite.

Still a further aspect of the present invention is a method of manufacturing a conjugate of the invention comprising (i) coupling the reagent (V) with at least one modified nucleosidic component (VII)

$$(N)_r\text{-}(L'')_m\text{-}RG2 \quad\quad\quad (VII)$$

wherein

N, r and n are as defined above,

L'' is a linker, m is 0 or 1, and

RG2 is a reactive group capable of reacting with RG1, particularly a Click-reactive group such as an alkyne group, thereby forming the conjugate, or (ii) coupling the reagent (V) with at least one modified nucleic acid building block (VIII)

$$BB\text{-}(L'')_m\text{-}RG2 \quad\quad\quad (VIII)$$

wherein

BB is a building block for synthesizing an nucleic acid molecule,

L'' is a linker, m is 0 or 1, and

RG2 is a reactive group capable of reacting with RG1, particularly a Click-reactive group such as an alkyne group, thereby forming the reagent (VI), and incorporating the reagent (VI) into an nucleic acid molecule, e.g. by chemical or enzymatic synthesis, thereby forming the conjugate.

A further aspect of the present invention relates to a method of mediating target-specific nucleic acid modifications in a cell or an organism comprising the steps:

(a) contacting a cell or organism with the conjugate of the invention, under conditions, wherein target-specific nucleic acid modifications may occur, and (b) mediating a target-specific nucleic acid modification effected by the nucleosidic component of the conjugate towards a target nucleic acid.

Contacting step (a) may comprise introducing the conjugate into a target cell, e.g. an isolated target cell, which may be present in a cell culture, a unicellular micro-organism, or a target cell, or a plurality of target cells within a multicellular organism. The target cell is preferably a mammalian cell, including a human cell. The target organism is preferably a mammalian organism, e.g. a human organism. The introducing into an organism may comprise parenteral administration, e.g. by injection or infusion, transmucosal administration or transdermal administration.

Mediating step (b) preferably comprises an inhibition of a target nucleic acid, e.g. by RNA interference when using an siRNA conjugate, or by inhibition of mRNA transcription when using an antisense molecule conjugate, or by inhibition of virus or tumor cell replication using a therapeutic nucleoside/nucleotide conjugate.

The conjugate is preferably introduced into a target cell by receptor-mediated endocytosis, more preferably by cannabinoid receptor-mediated endocytosis. Thus, the conjugate may be introduced into the target in the absence of a delivery vehicle and/or a transfection reagent.

In one embodiment, the conjugate of the invention is for use in the transfection of cells in vitro, particularly for the transfection of mammalian cells, including human cells in vitro. Surprisingly it has been found that the conjugate of the invention is particularly suitable for the transfection of immune cells such as B-cells, T-cells, macrophages, natural killer cells and precursors thereof, as well as neuronal cells, astrocytes or other cells expressing the cannabinoid receptor. Examples of immune cells expressing the cannabinoid receptor CB2 are described in (49, 50 and 51), the contents of which are herein incorporated by reference. Examples of neuronal cells expressing the cannabinoid receptor CB1 are described in (52, 53, 54 and 55), the contents of which are herein incorporated by reference.

In a further embodiment the conjugate of the present invention is for use in medicine, particularly in human medicine, but also in veterinary medicine. Thus, the present invention also provides a pharmaceutical composition comprising a conjugate as described above as the active ingredient together with a suitable carrier. For diagnostic or therapeutic applications, the pharmaceutical composition may be in the form of a solution, e.g. a solution for infusion or injection, a cream, ointment, tablet, suspension or the like. The composition may be administered in any suitable way, e.g. by parenteral administration, e.g. injection or infusion, by transmucosal application, or by transdermal application, or by oral, topical, nasal, rectal application, etc.

The pharmaceutical composition may comprise the conjugate as an active agent in non-encapsulated form, e.g. without a delivery vehicle such as a liposome and/or without a transfection reagent.

The conjugate of the present invention may be used for the down-regulation of genes in a cell or an organism, e.g. viral genes or cellular disease-associated genes, such as oncogenes, or autoimmune or allergic disease-associated genes. Preferred cellular target genes are e.g. the syk gene, which is an autoimmune or allergic disease-associated gene encoding a spleen tyrosine kinase (SYK), which is involved in IgE-dependent inflammatory signalling cascades. The human SYK ortholog is described in UniProt P 43405, the murine SYK ortholog is described in UniProt P 48025. A further preferred target gene is the APP gene which encodes the amyloid precursor protein (APP). The human APP ortholog is described in UniProt P 05067. APP is cleaved by β- or γ secretases into neurotoxic fragments associated with the development of Alzheimer's disease. Preferred viral target genes are genes encoding the N or P protein of viruses of the mononegavirales order such as Ebola virus, measles virus and rabies virus.

Further aspects of the invention are as described in the following. Specific features and combinations of features of these aspects may be derived from the disclosure of the above aspects.

A conjugate comprising a receptor ligand component, e.g. a polyunsaturated fatty acid residue, a folate, a cholesterol or a hormone as described above, and covalently bound thereto at least one nucleosidic component as described above, wherein the conjugate comprises one receptor ligand component and at least 2 molecules of the nucleosidic component, e.g. 2, 3, 4, 5, 6, 7 or 8 molecules.

A conjugate comprising a receptor ligand component, e.g. a polyunsaturated fatty acid residue, a folate, a cholesterol or a hormone as described above, and covalently bound thereto at least one nucleosidic component as described above, wherein the receptor ligand component is bound to the nucleosidic component via linker which comprises a group formed by a Click reaction, e.g. a 1, 2, 3-triazole group as described above.

A conjugate comprising at least one C=C unsaturated compound and covalently bound thereto at least one nucleosidic component as described above, wherein the C=C unsaturated compound is bound to the nucleosidic component via linker which comprises a group formed by a Click reaction, e.g. a 1, 2, 3-triazole group as described above. The C=C unsaturated compound comprises at least one C=C bond, particularly a C=C bond in the Z-configuration. Preferred examples are terpenes and unsaturated fatty acids, e.g. mono- or polyunsaturated fatty acids.

The C=C unsaturated compound preferably is a C4-C24 compound, particularly a fatty acid including derivatives thereof, e.g. a jasmonate such as jasmonic acid or a jasmonate ester, for example a jasmonate methyl ester.

In some embodiments, the C=C unsaturated compound comprises a single C=C bond, particularly in the Z-configuration.

The present invention shall be outlined in more detail by the following Figures and Examples.

FIGURE LEGENDS

FIG. 1

Synthesis of azide modified anandamide (1) as well as folate (2) and cholesterol (3) derivatives.

5=11-azido-3,6,9-trioxaundecan-1-amine,

PyBOP=benzotriazol-1-yloxytripyrrolidinophosphonium hexafluorophosphate,

TBTU=O-(benzotriazol-1-yl)-N,N,N',N'-tetramethyluronium tetra-fluoroborate,

DIPEA=N,N-diisopropylethylamine,

DBU=1,8-diazabicyclo [5.4.0]undec-7-ene,

9=pteroic acid,

TFA=trifluoroacetic acid, and

CDI=carbonyldiimidazol

FIG. 2

Chemical structure and sequence of anandamide and folate modified siRNA targeting Renilla Luciferase.

FIG. 3

Delivery of fluorescein labeled siRNA and dsDNA to RBL-2H3 and HeLa cells. Cannabinoid receptor expressing RBL-2H3 cells were incubated with anandamide (AEA) modified dsDNA and siRNA. Folate receptor expressing HeLa cells incubated with folate (FA) modified dsDNA and siRNA. As a negative control both cell lines were incubated with duplexes lacking a ligand modification.

FIG. 4 a, b) Relative silencing of Renilla luciferase mediated by folate (FA, violet) modified siRNA in HeLa cells and by anandamide (AEA, blue) modified siRNA in RBL-2H3 cells. Quantification via luciferase activity. c) Relative silencing of Renilla luciferase mediated by cholesterol (Chol, green) and anandamide (AEA, blue) modified siRNA in RBL-2H3 cells. Quantification via luciferase activity. d) Relative silencing of spleen tyrosine kinase mediated by cholesterol (Chol, green) and anandamide (AEA, blue) modified siRNA in RBL-2H3 cells. Quantification was carried out by determining the mRNA level.

FIG. 5

Relative silencing of luciferase mediated by anandamide (AEA, blue) modified siRNA and by jet PRIME (JP, grey) encapsulated non-modified siRNA in human B-cells (BJAB). The gene silencing effect of the AEA modified siRNAs is similar to the jet prime-encapsulated siRNAs.

FIG. 6

The cytotoxicity of anandamide (AEA, blue) modified siRNA and jet PRIME-encapsulated siRNA (JP, grey) is shown. Quantification via cytotox-Gio cytotoxicity assay (Promega). Normal cell growth (mock, black) and induced cell death (pos. C, red) are also shown. AEA-modified siRNA does not exhibit cytotoxicity in a concentration of 1.0 µM. In contrast thereto, jet PRIME-encapsulated siRNA shows a dose-dependent increase in cytotoxicity.

FIG. 7

Comparison of different anandamide-modified siRNAs.

a) Conjugate of anandamide (AEA ligand), linker and a single siRNA molecule.

b) Conjugate of an AEA-ligand, a branched linker and three siRNA molecules.

FIG. 8 a) 9-fold azide modified anandamide conjugate as a reagent for producing a 9-fold siRNA modified anandamide.

b) Scheme for covalent coupling of alkyne-modified RNA oligonucleotides to a 9-fold alkyne-azide-modified anandamide via copper-catalysed alkyne-azide Click reaction (CuAAC).

FIG. 9 a, b) Exemplary synthesis of 9-fold azide-modified anandamide constructs.

FIG. 10

Characterisation of 9-fold and 8-fold anandamide-modified RNA oligonucleotide via HPLC and mass spectrometry.

FIG. 11

Comparison of siRNA efficacy of different anandamide (AEA)-modified RNA constructs with 1, 3, 7, 8 and 9 siRNA molecules. Quantification via luciferase activity. The highest efficacy was found with constructs having 3 and 7 siRNA molecules per receptor ligand.

FIG. 12

Comparison of the efficacy of down-regulation of an endogenous gene (SYK) with conjugates having 1, 3, 8 or 9 siRNA molecules per construct.

The construct with 3 siRNA molecules per anandamide shows the best results.

EXAMPLES

1. Synthesis of RNA-Ligand Conjugates

The synthesis of the anandamide modified RNA strand was performed as depicted in FIG. 1. The central element of the synthesis is the Cu-catalyzed alkyne-azide click reaction (34-39) between an alkyne modified RNA strand and the corresponding ligand azides 1. In order to compare the anandamide modified RNA strands to other systems, we utilized the click method also for the preparation of a folate-RNA (40) conjugate using folate azide 2 and of cholesterol modified RNA strand with the cholesterol azide 3. We introduced in all cases a short tetraethylene glycol spacer between the RNA strand and the respective ligand. The click-technology enabled in all cases efficient ligation of the hydrophobic and often quite insoluble (folate) ligand molecules to RNA. In addition, the method enabled efficient conjugation at the more difficult to access 3'-terminus of the siRNA duplex. 3'-modified siRNA strands that are typically better tolerated by the RNAi machinery (41). To achieve the 3'-end attachment we used a deoxyuridine phosphoramidite with an octadiine handle at C5 during RNA synthesis.

Figure 2:
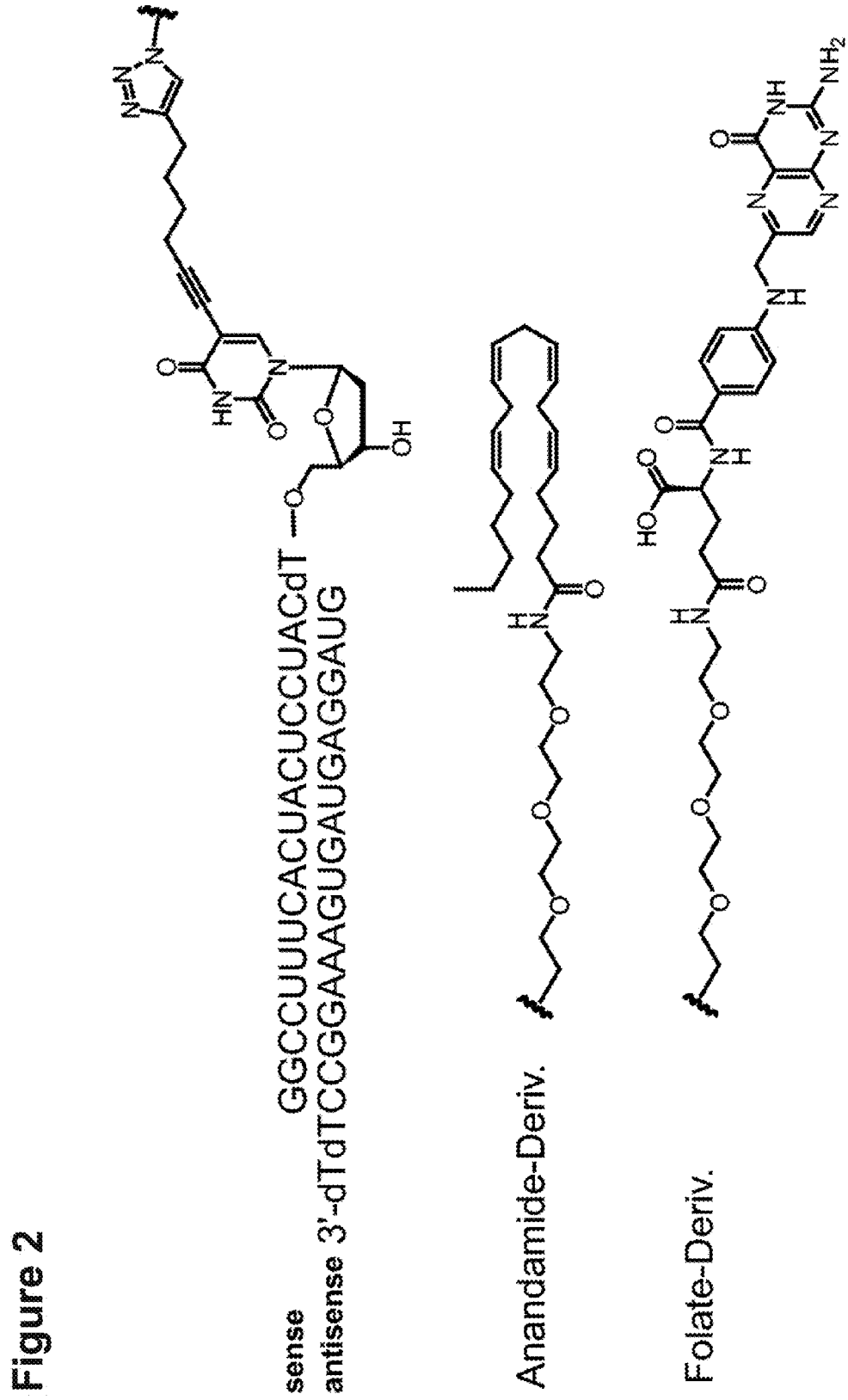

The anandamide azide ligand 1 was prepared in just one step from arachidonic acid 4 and the azido- and amino-functionalized oligoethylene glycol 5. The same strategy was employed for the synthesis of the cholesterol azide 3. The folate derivative 2 was prepared via a slightly more elaborate synthesis starting with the protected glutamic acid derivative 6, which was condensed with the amino-azide tetraethylene glycol compound 5. Cleavage of the Fmoc group and coupling with pteroic acid furnished after deprotection of folate 2. Compound 2 contains in this way the ethylene glycol spacer attached to the gamma-carboxyl group, which provides a folate compound with superior receptor binding properties (42). The three azides were subsequently clicked with excellent yields to the alkyne containing RNA sense strand. After HPLC purification, the ligand modified RNAs were hybridized to the antisense counterstrand to obtain the siRNA duplexes depicted in FIG. 2.

2. Delivery of RNA-Ligand Conjugate Into Cells

Figure 3:
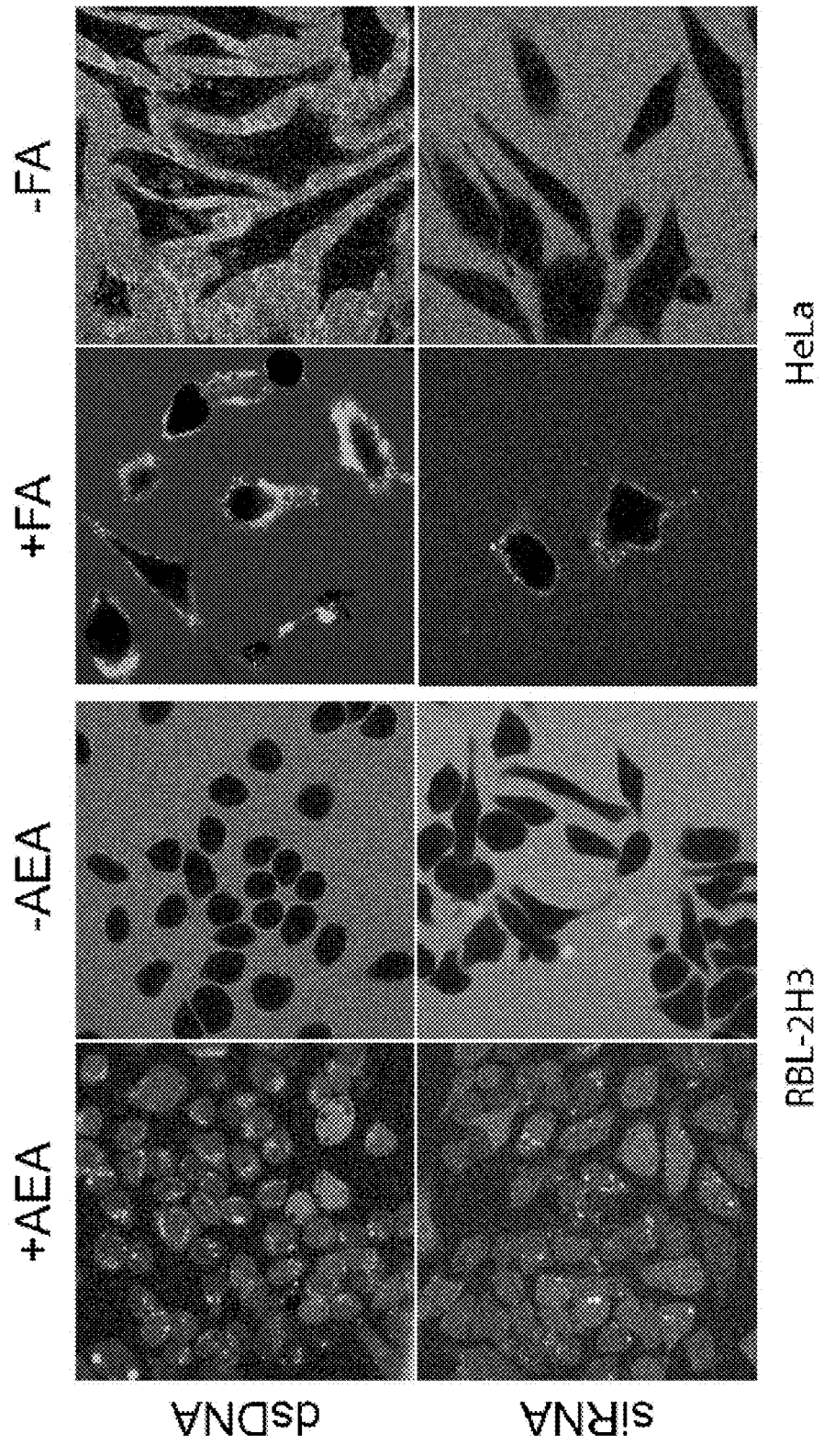

In order to visualize the delivery of the RNA duplexes into living cells we initially hybridized the anandamide- and folate-modified RNA sense strand to an antisense strand containing a fluorescein label. FIG. 3 shows the result of confocal microscopy studies performed with two different cells lines. For the anandamide modified RNA duplex we utilized RBL-2H3 cells, which serve as a model for immune cell function (43). Barker et al. were able to show that the uptake of anandamide by RBL-2H3 cells is functionally identical to neuronal cells and astrocytes (44). Thus this cell line is an excellent model for anandamide uptake in immune cells and neurons.

Uptake of the folate modified RNA duplex was studied with HeLa cancer cells known to overexpress the folate receptor. The microscopy studies showed that unmodified siRNA is as expected unable to enter both cell lines. Anandamide and folate modified siRNA however were readily detected inside the respective cells proving uptake. The same result was also observed with modified dsDNA which shows that the uptake is entirely ligand dependent (FIG. 3).

Figure 4:
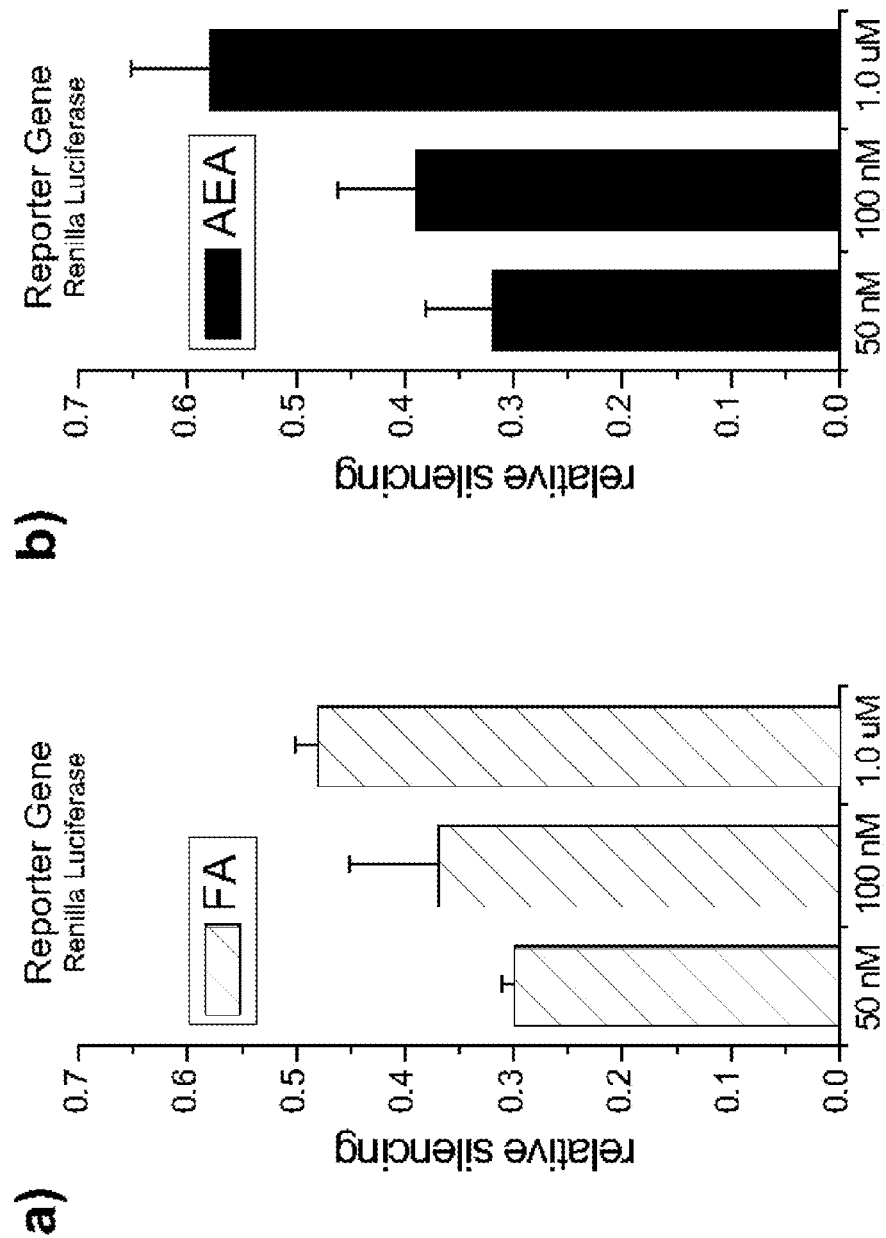
Figure 4:
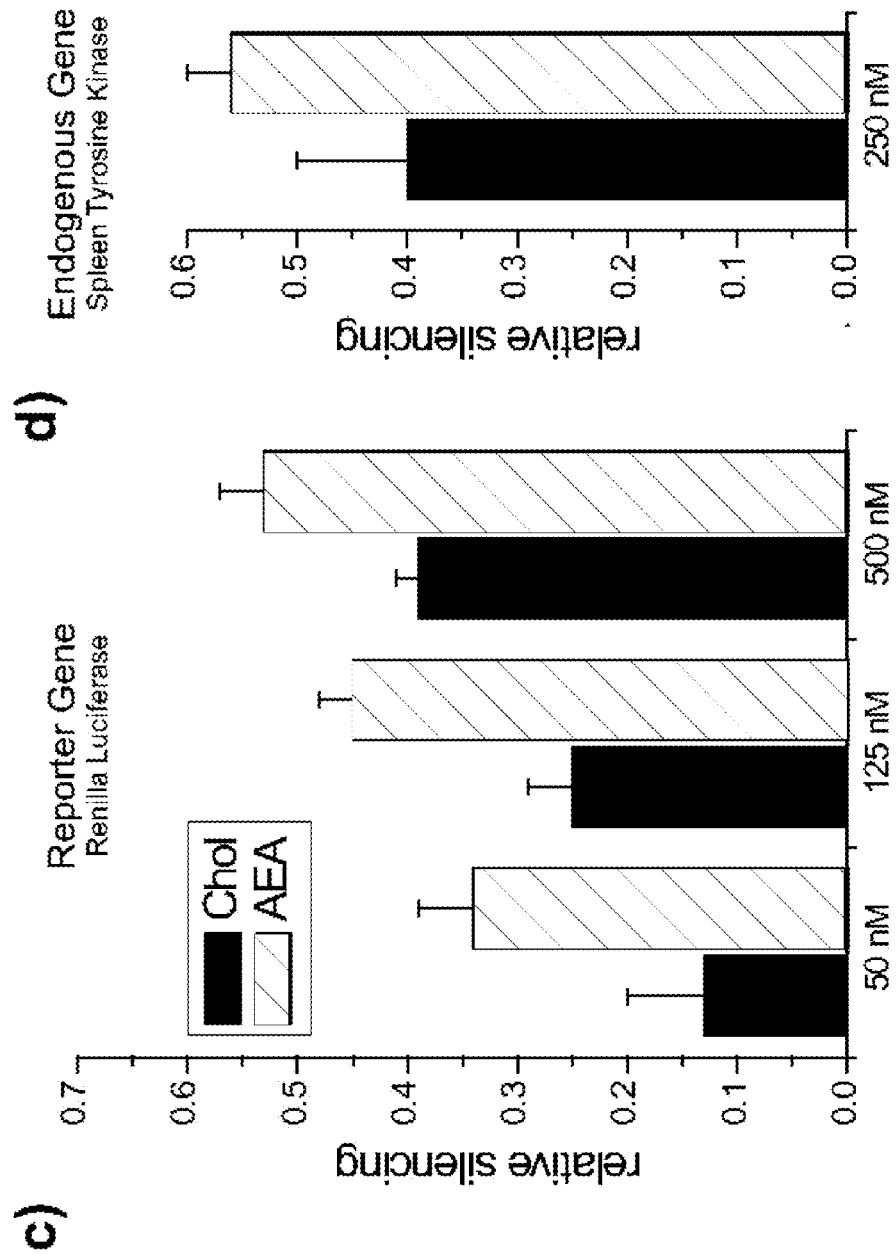
Figure 5:
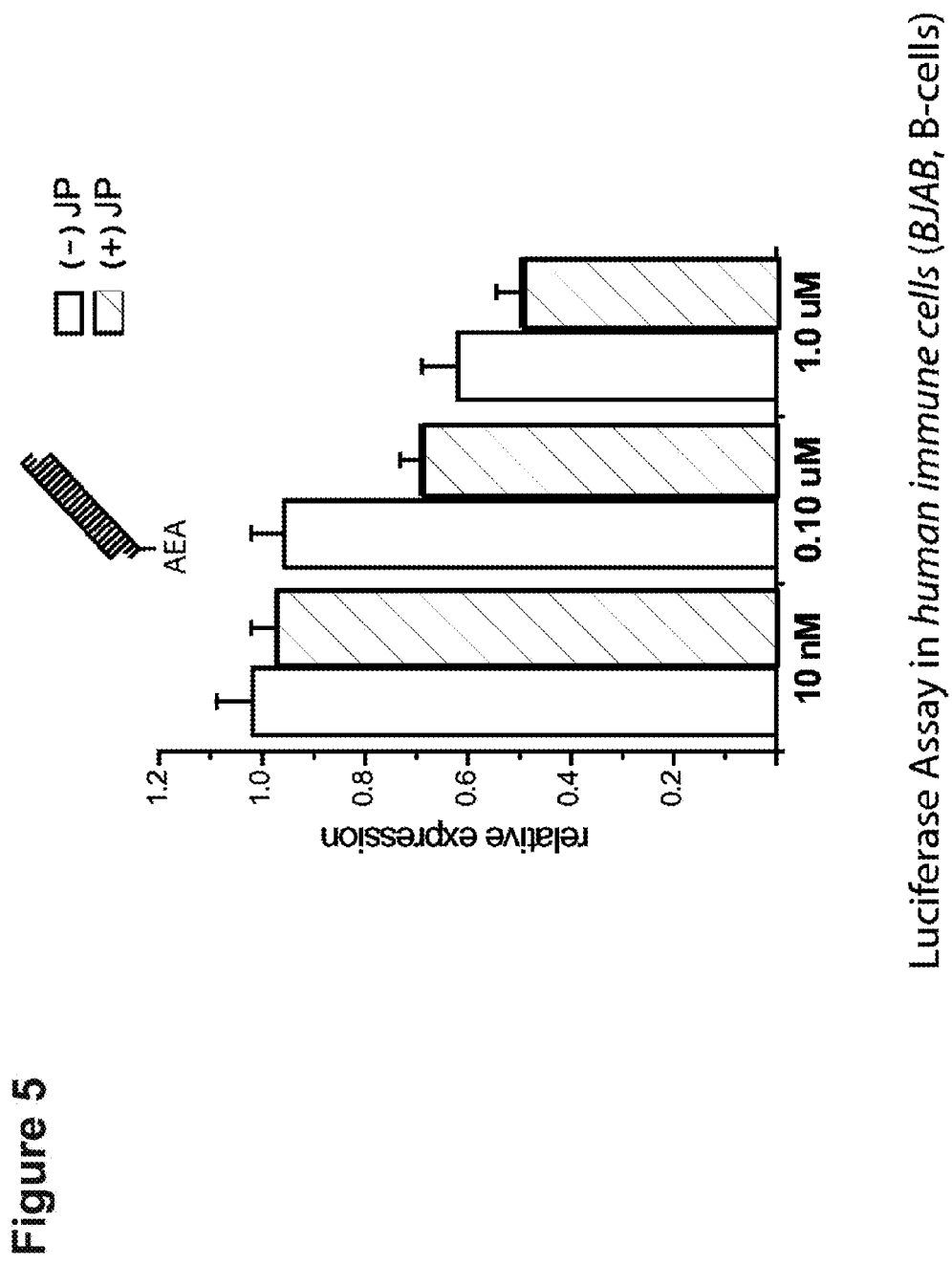
Figure 6:
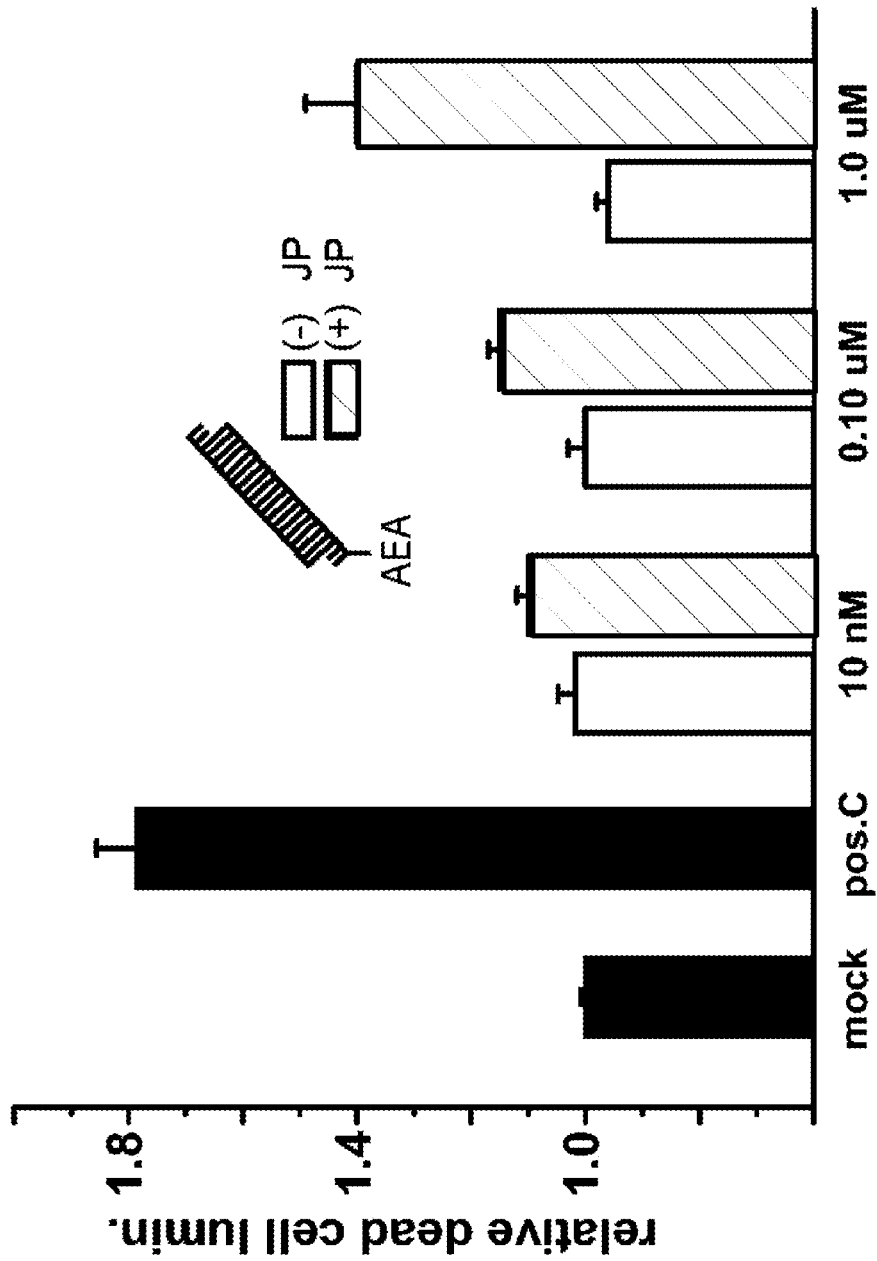
Figure 7A:
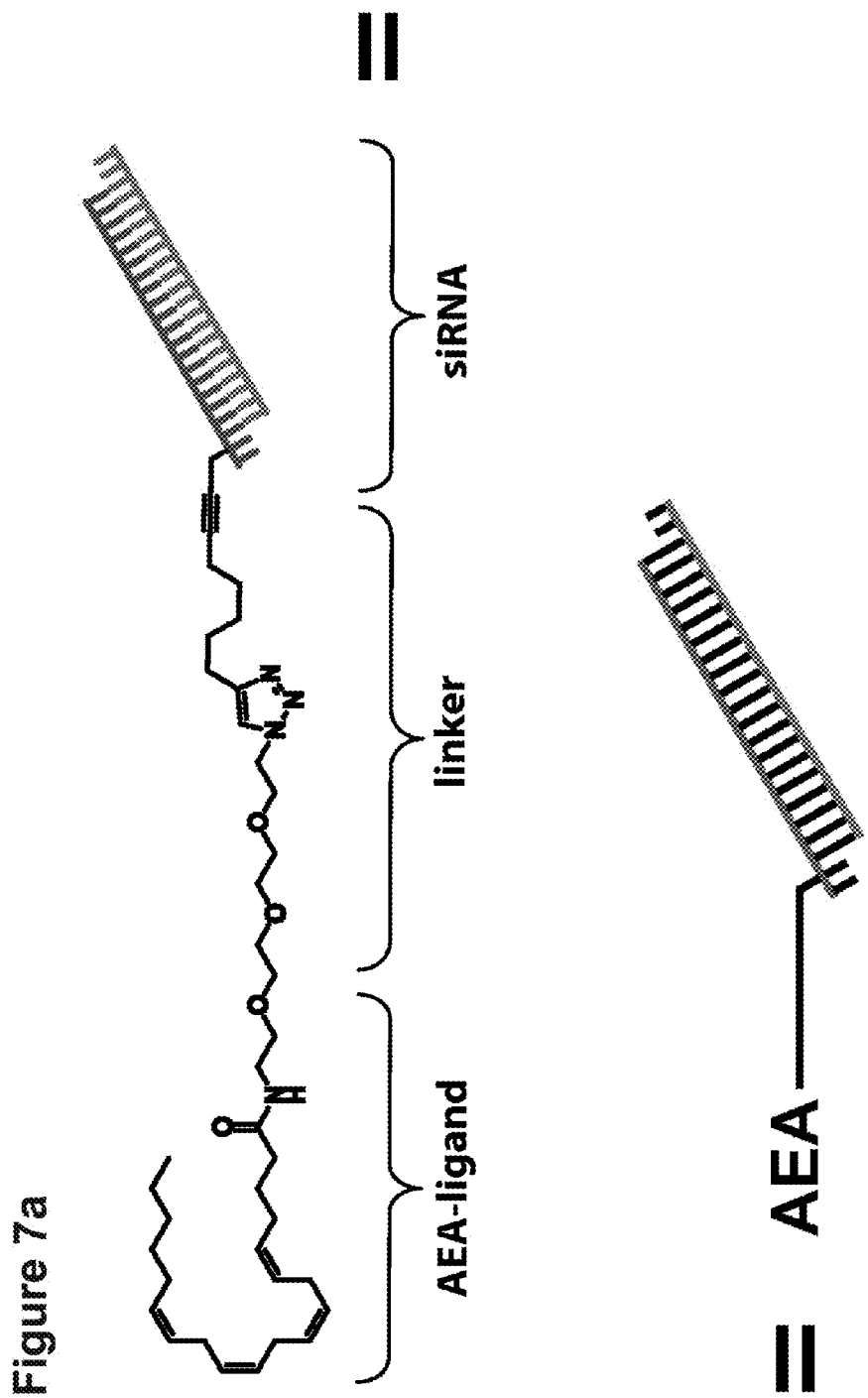
Figure 7B:
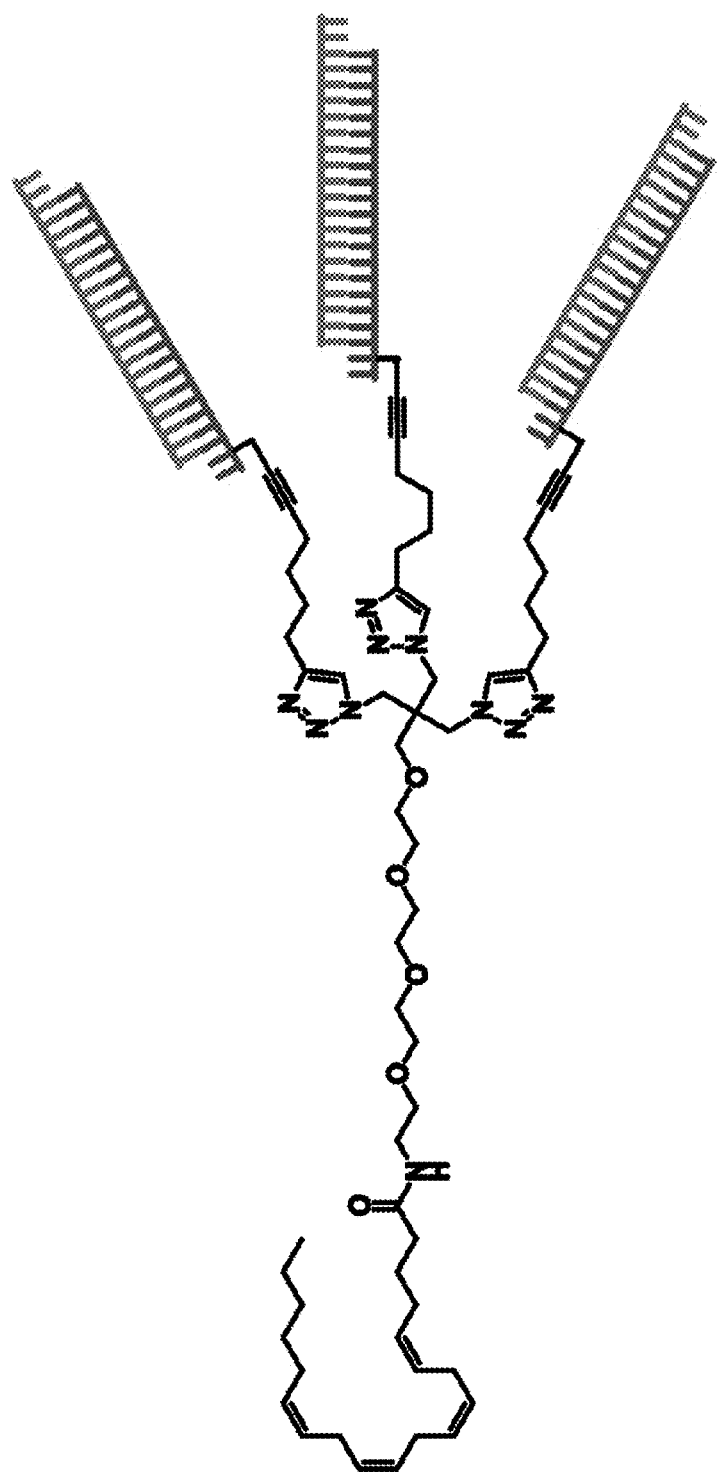
Figure 7B:
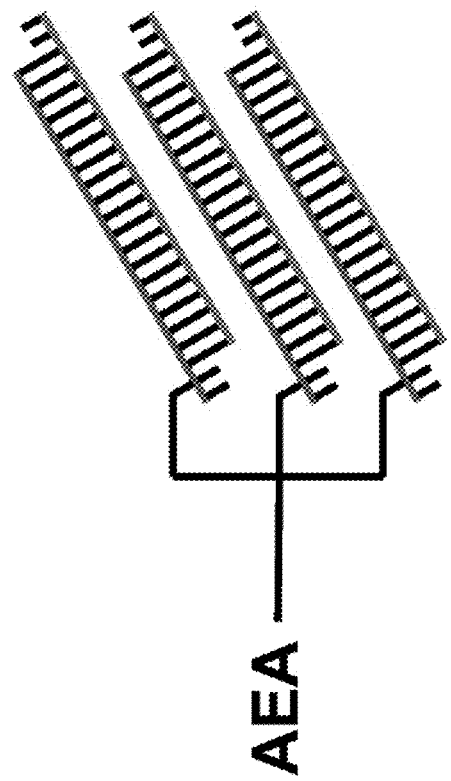
Figure 8A:
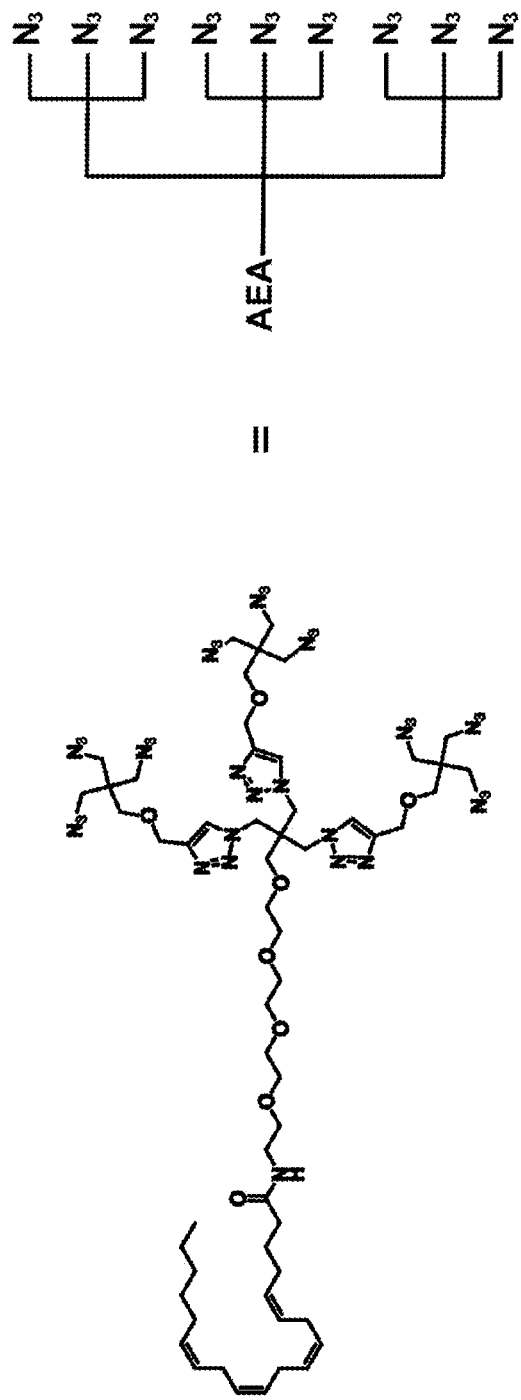
Figure 8B:
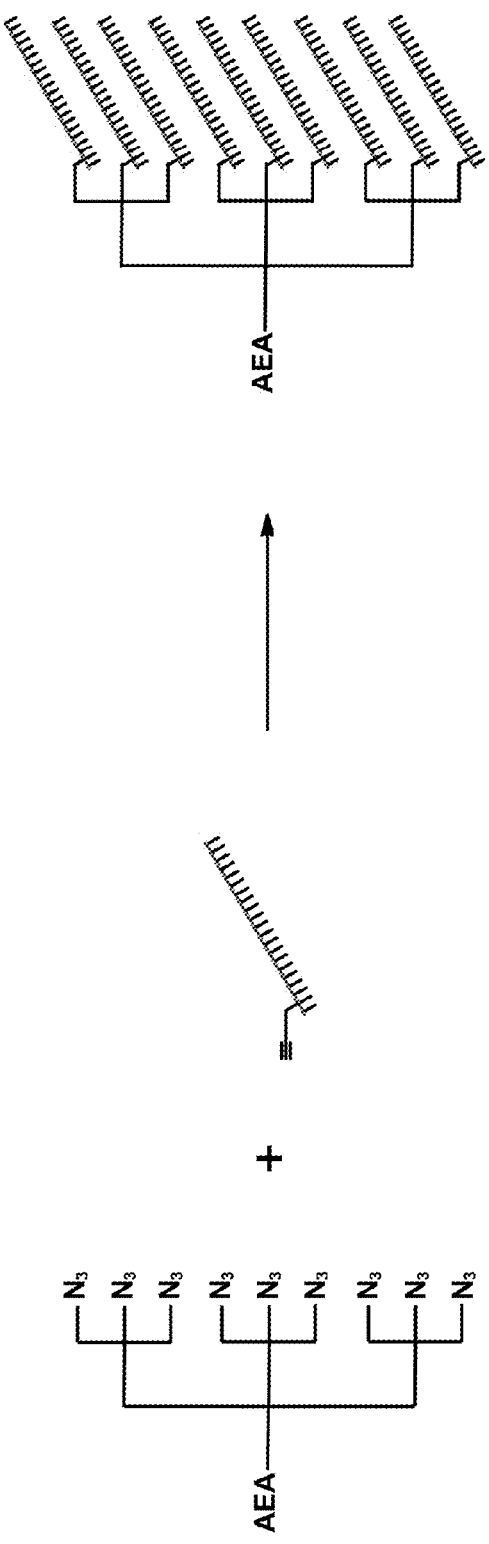
Figure 9A:
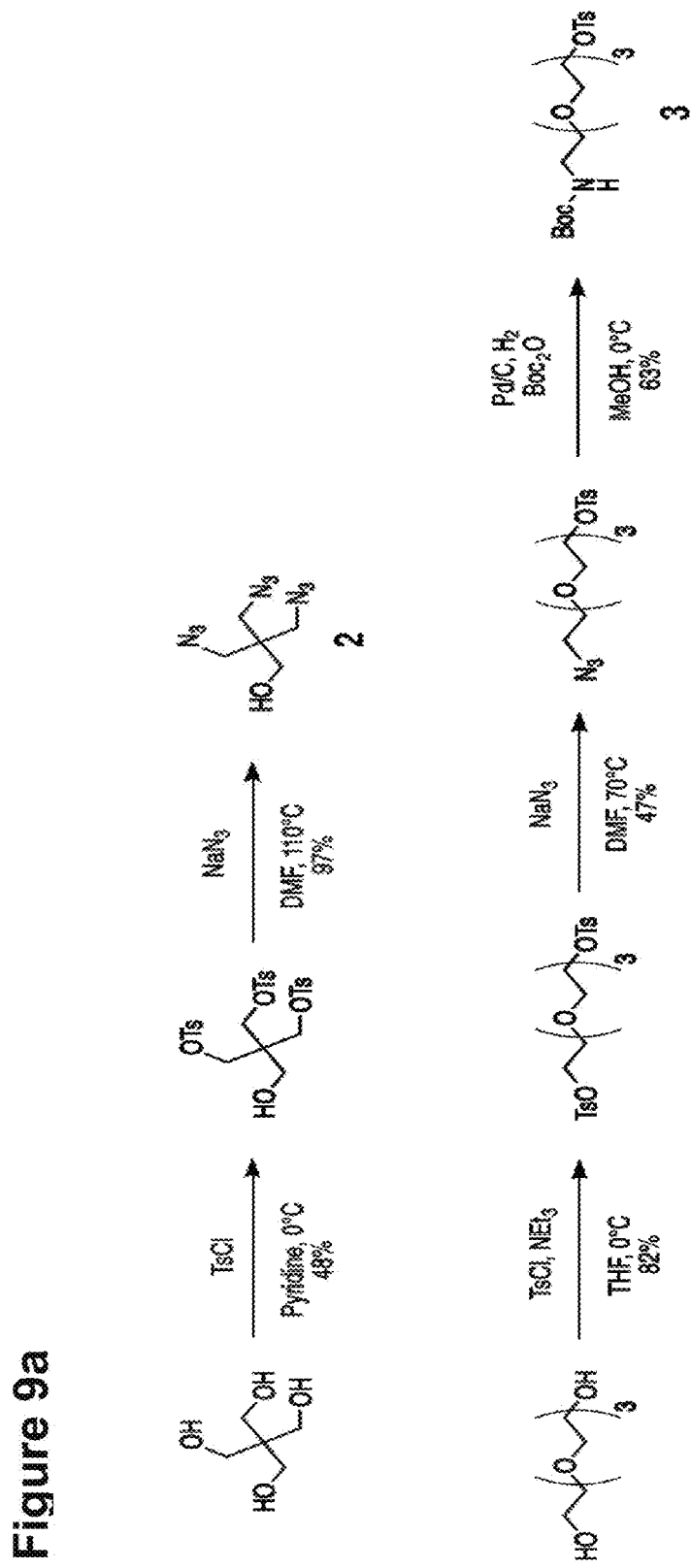
Figure 9A:
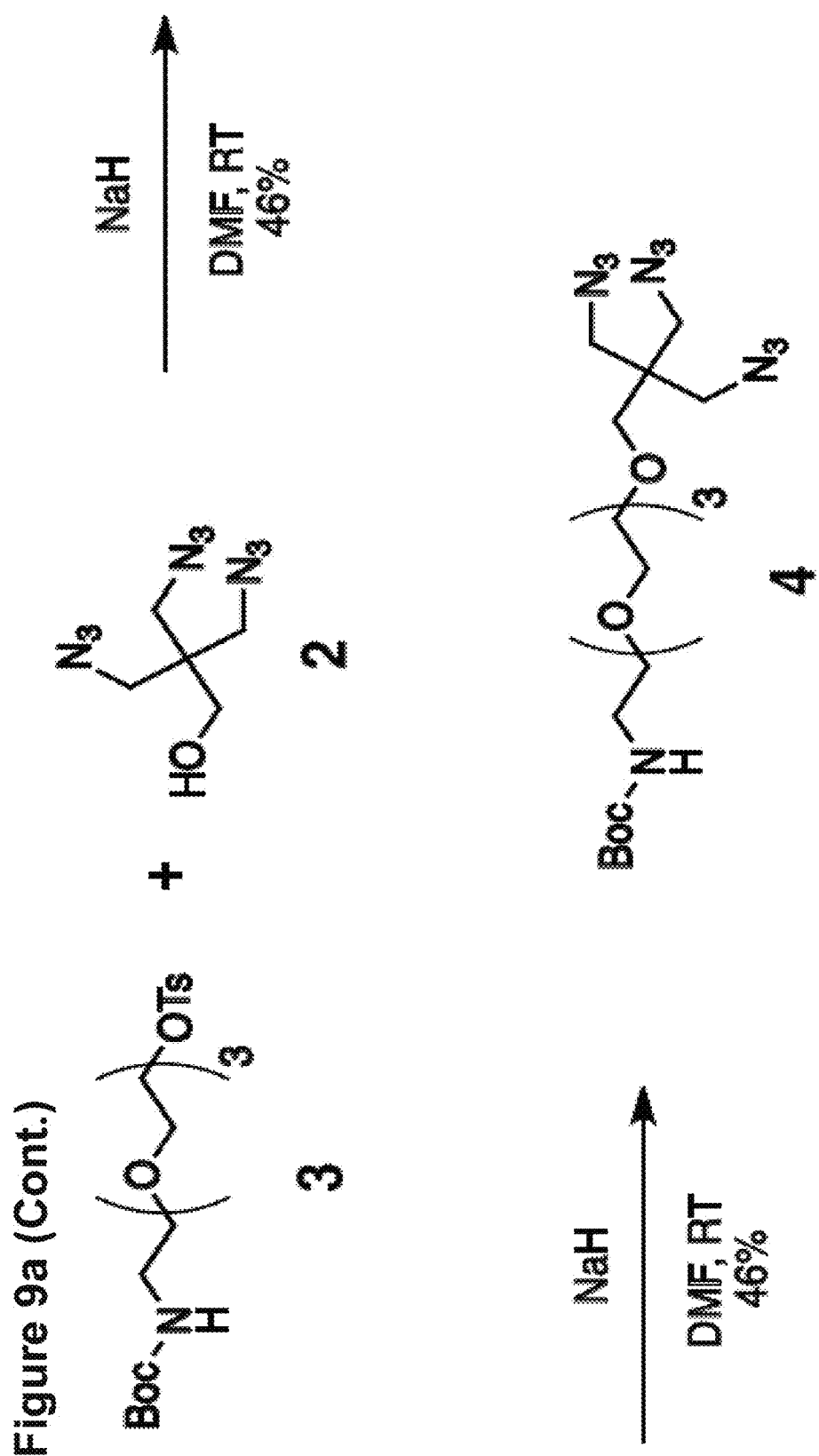
Figure 9B:
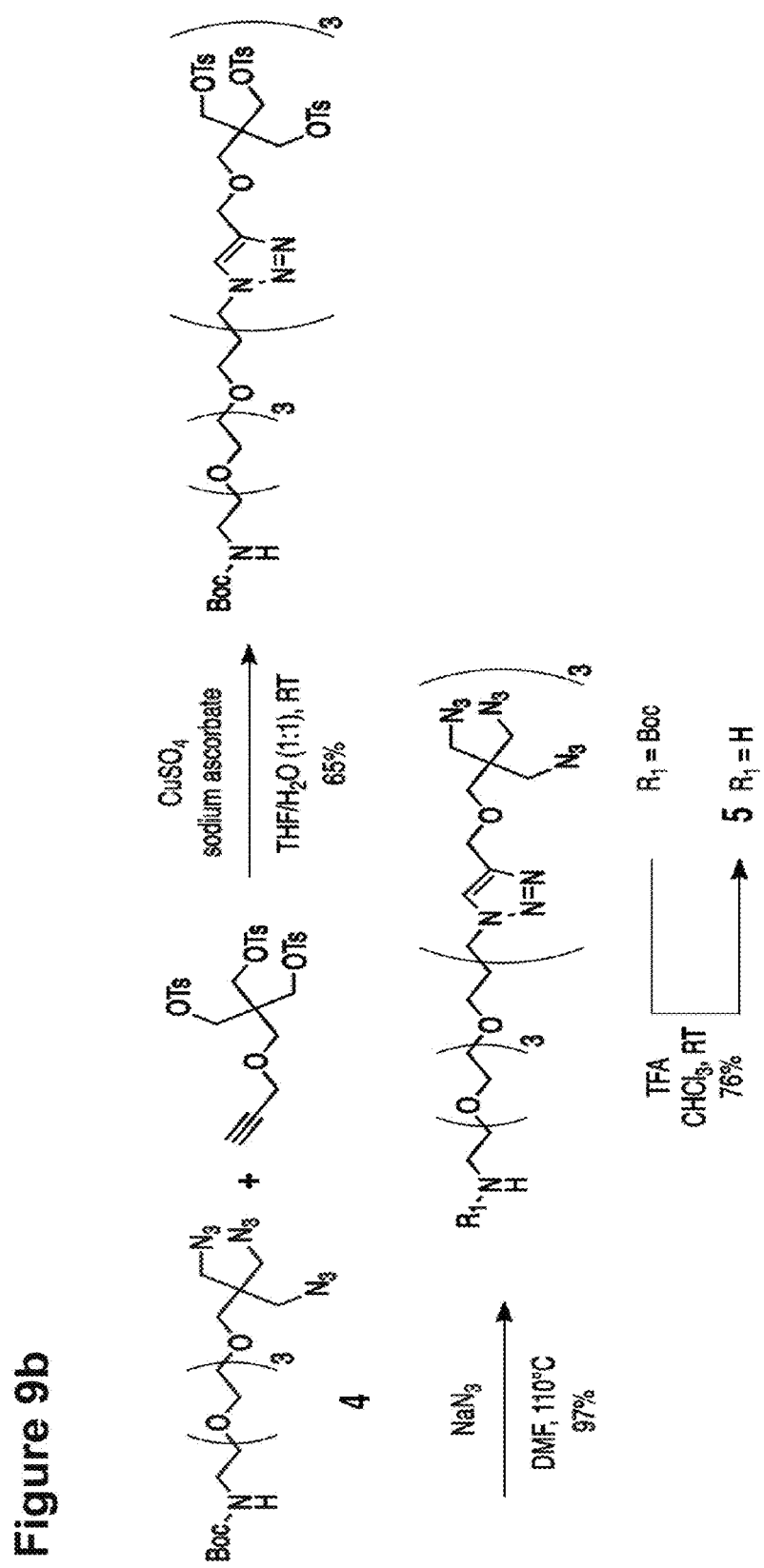
Figure 9B:
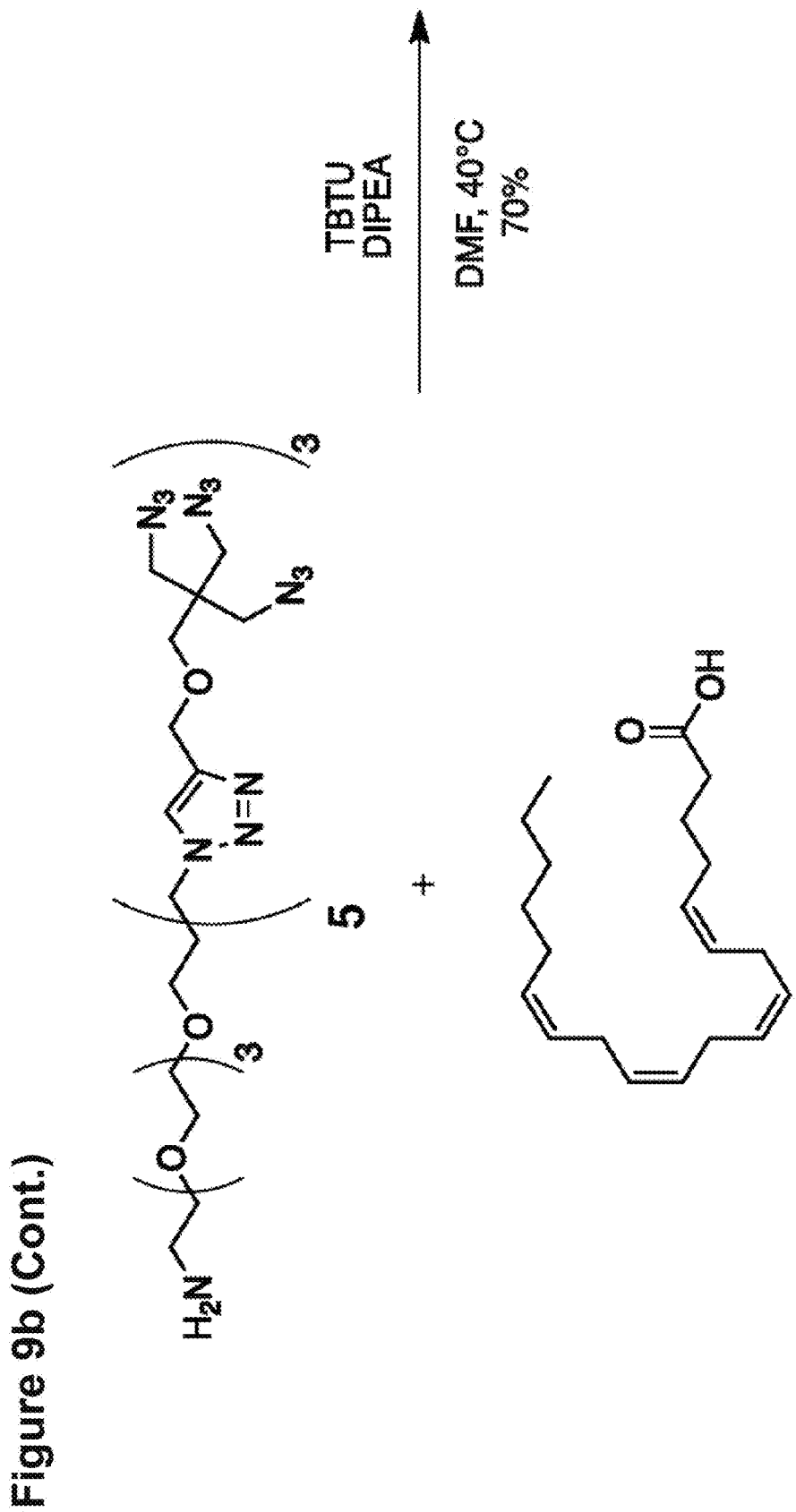
Figure 9B:
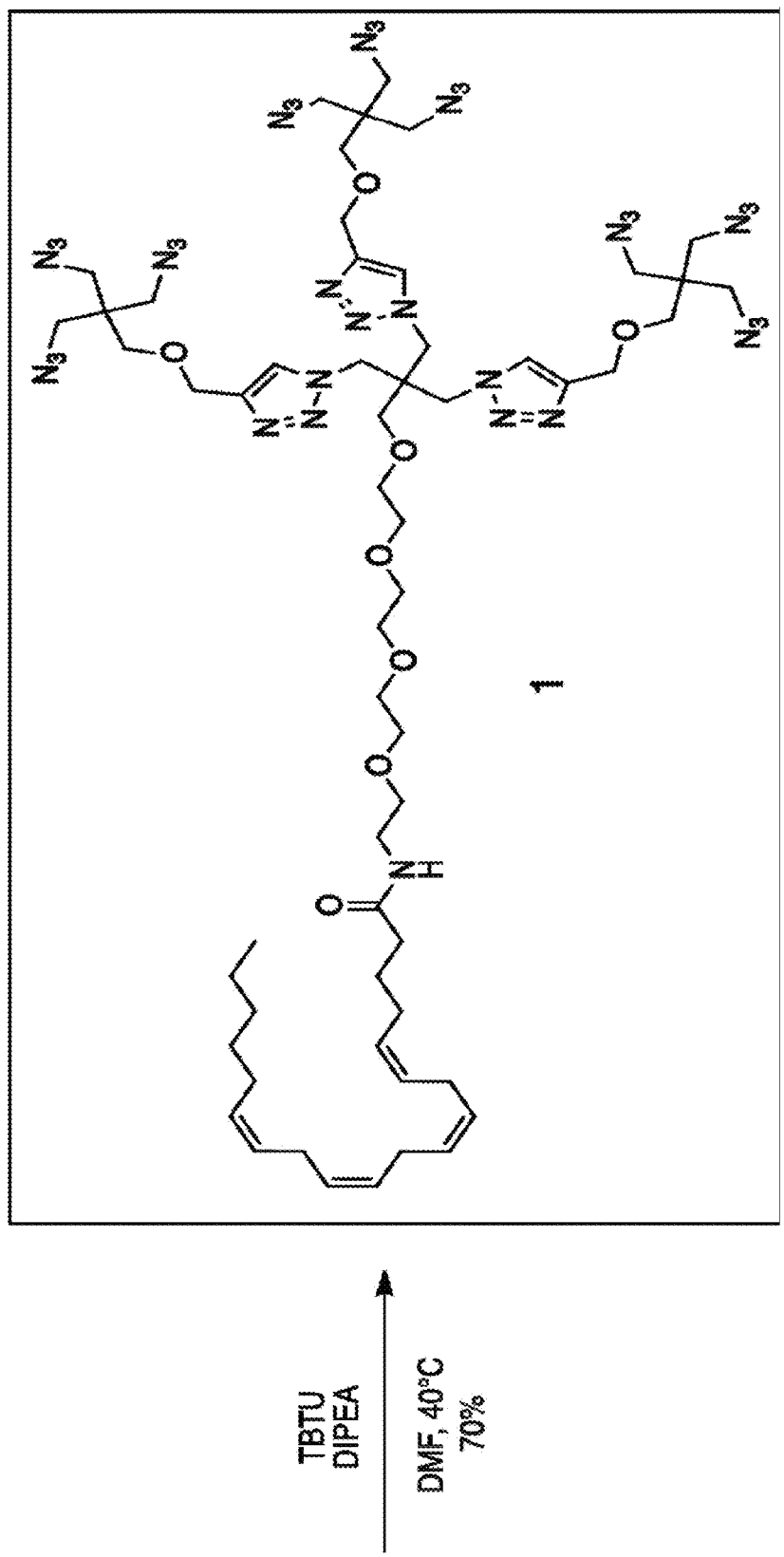
Figure 10:
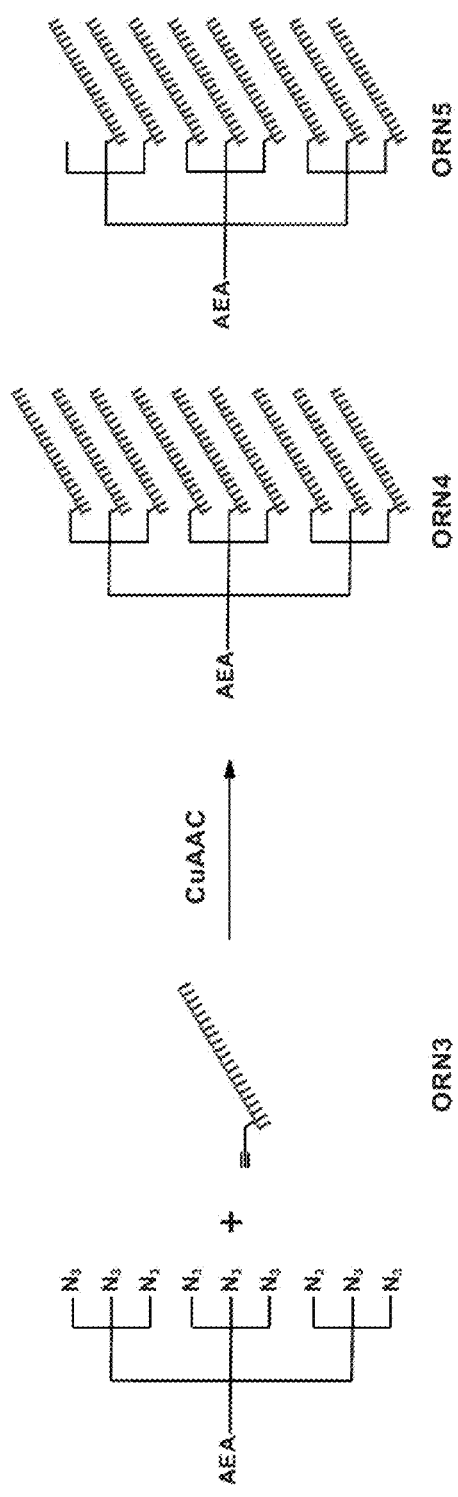
Figure 10:
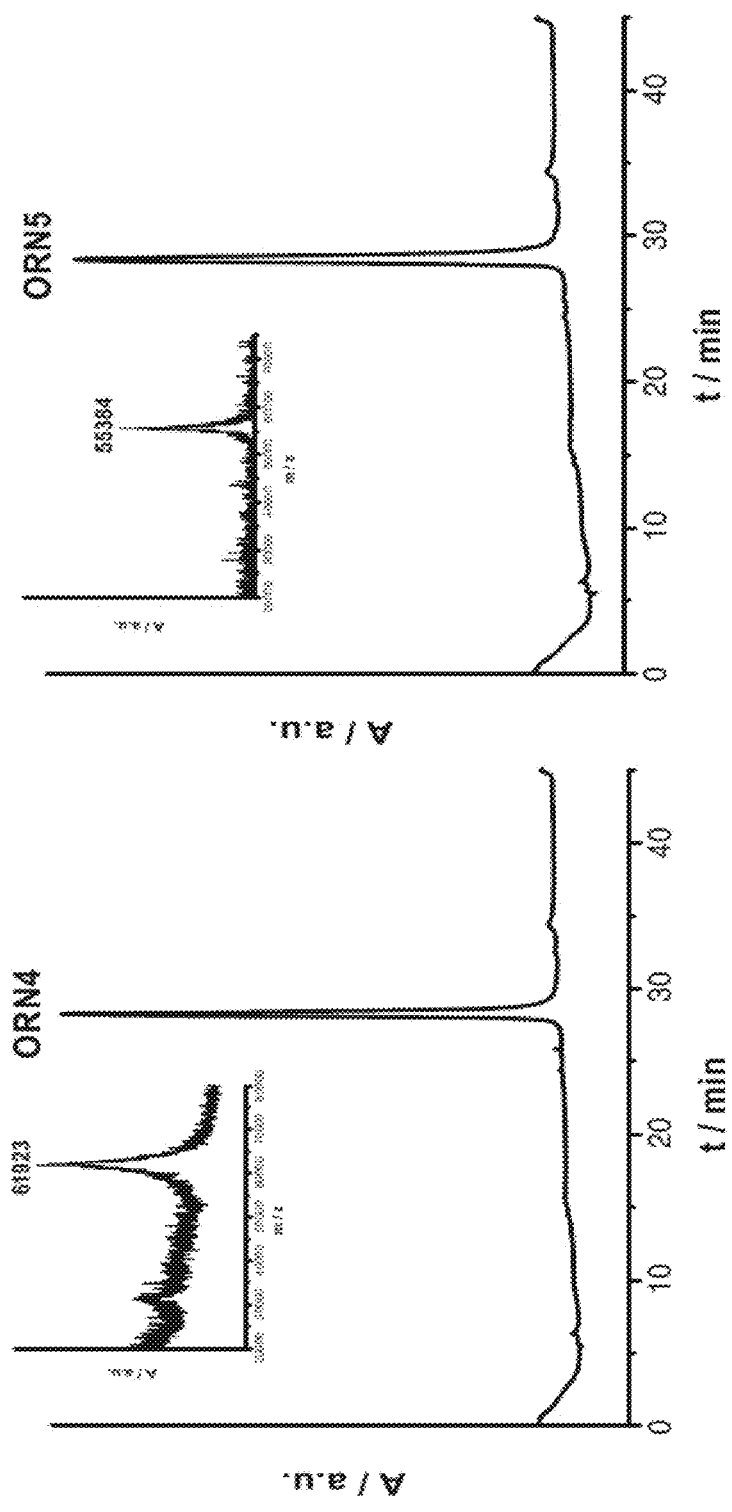
Figure 11:
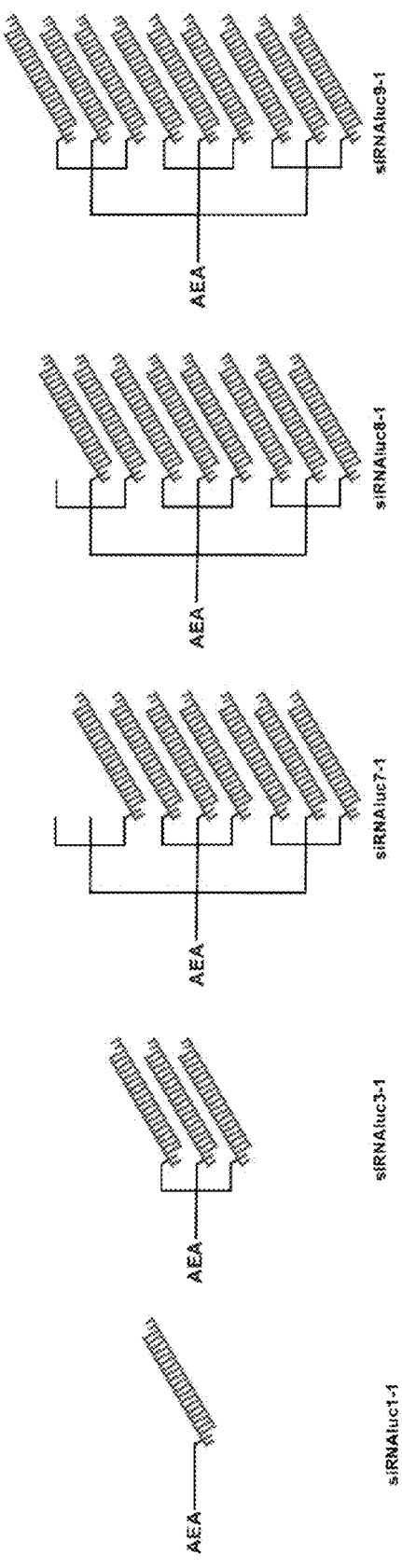
Figure 11:
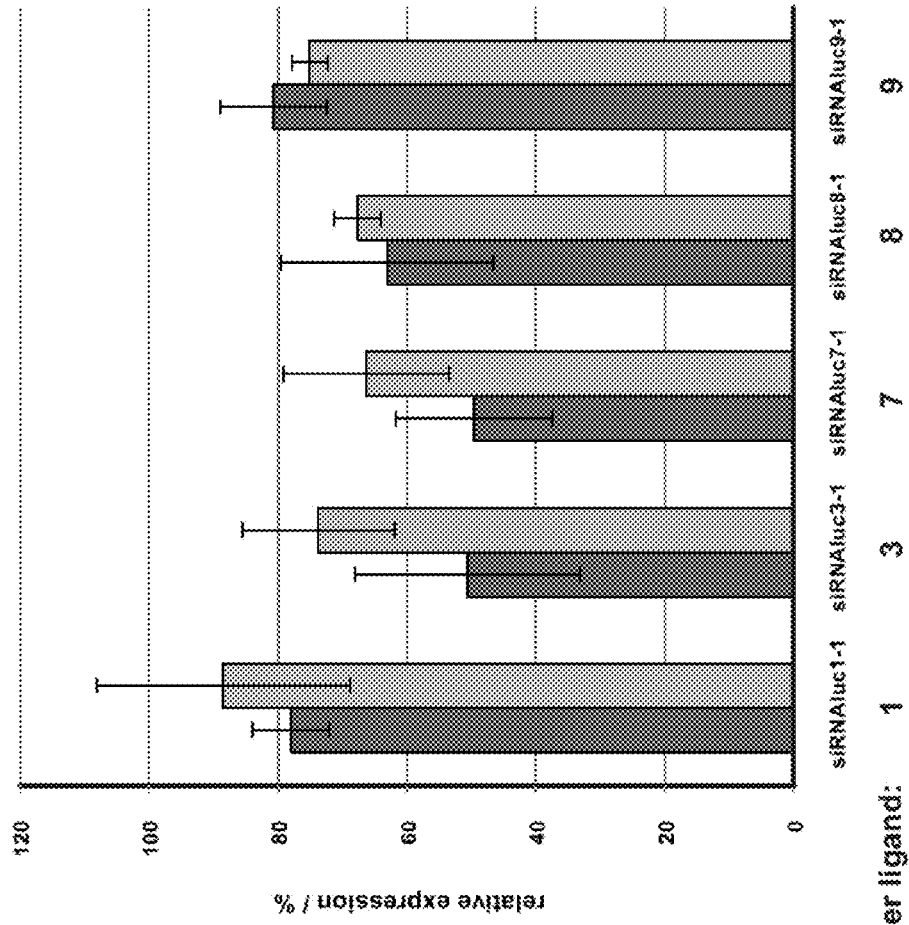
Figure 12:
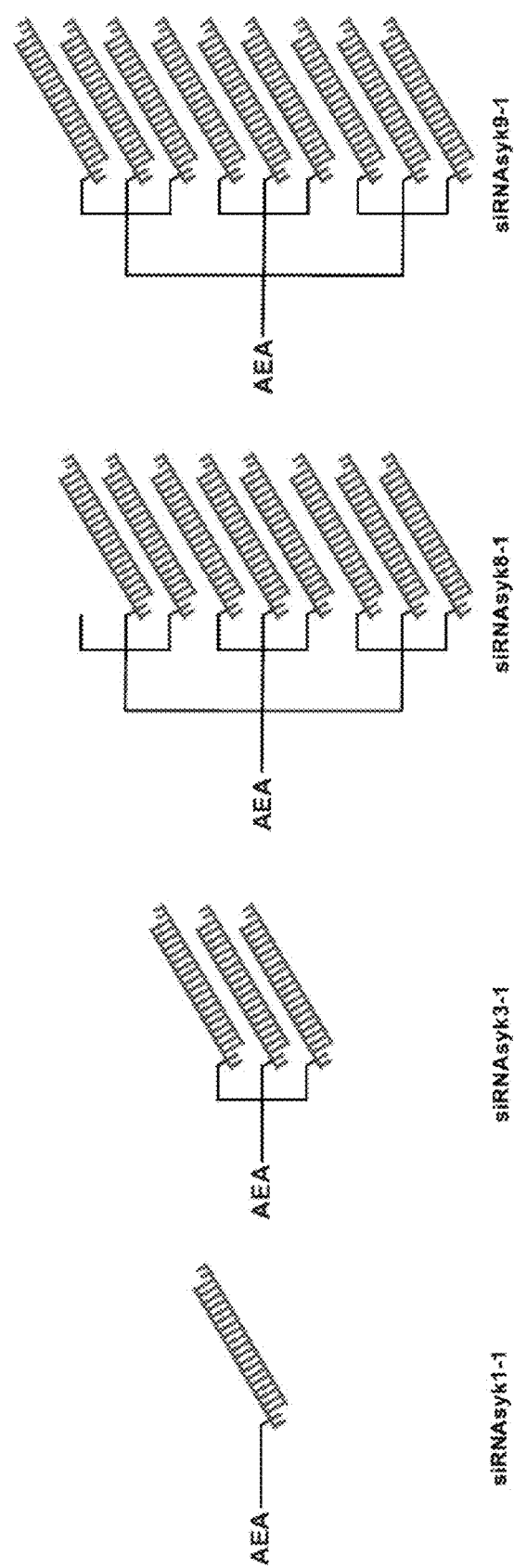
Figure 12:
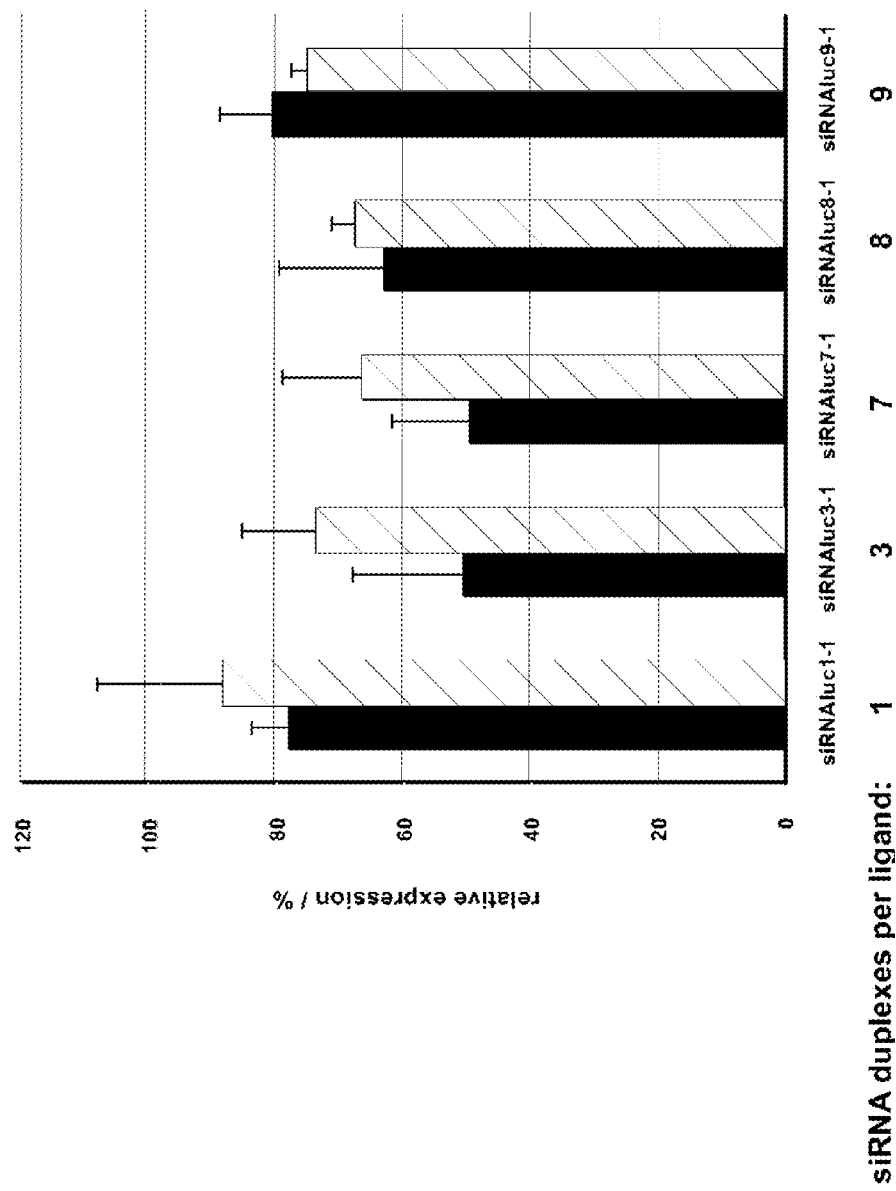

To demonstrate that the delivered siRNA molecules exhibit the desired RNAi effect we utilized a commercially available dual-luciferase reporter assay. A plasmid containing two luciferases (Renilla and Firefly) was transfected into the cells. RNAi was evaluated by targeting the expression of the Renilla luciferase, whereas the Firefly luciferase served as an internal standard. For these studies we used the ligand modified siRNA without further fluorescein modification. Initial control experiments with unmodified RNA duplexes (no ligand, no fluorescein) showed that the Renilla expression was not affected. In contrast, we observed a dose dependent silencing of Renilla expression in presence of ligand modified siRNA in both cell lines (FIG. 4). Most important, even a relatively low amount of siRNA-ligand conjugate showed already a considerable effect that finally leads to a relative silencing of about 60%.

A final control experiment was performed with a scrambled siRNA. Here again we were unable to detect any luminescence reduction showing that the observed silencing is caused by specific binding of anandamide modified siRNA to the mRNA target.

The silencing efficacy of anandamide modified siRNA was next evaluated in comparison to the cholesterol-siRNA conjugate (24). The result of this comparison is depicted in FIG. 4. To our surprise we noted that the new anandamide 1 modified siRNA is constantly significantly more potent than the broadly exploited cholesterol system, which establishes the anandamide ligand as a powerful new delivery tool.

In order to investigate if the anandamide-siRNA conjugate is able to down-regulate a therapeutically important endogenous gene product, we next attempted to suppress the expression of the spleen tyrosine kinase (SYK), which is a key protein involved in the IgE-dependent inflammatory signalling cascades. As such the protein is a prospective target for the treatment of allergic and inflammatory disorders (45,46). For the experiment we prepared an ananamide modified siRNA having the sequence described by Sanderson et al. (47). After addition of the siRNA conjugate to RBL-2H3 cells we monitored the expression level using real-time PCR. Indeed, the expression of the SYK protein was successfully reduced by about 55% (FIG. 4) and again the anandamide conjugate was found to be substantially more active than cholesterol modified siRNA.

In summary, we report here the use of the Cu-catalyzed alkyne-azide chemistry for the construction of novel anandamide siRNA conjugates. The chemistry enables the efficient construction of different ligand modified RNAs at the 3'-end in excellent yield and purity. This is particularly noteworthy for folate modified oligonucleotides which are notoriously difficult to access. The anandamide conjugation allowed transfection of immune cells and provides excellent silencing data. We believe that the anandamide ligand, in combination with click chemistry, has the potential to become the new gold standard for the transfection of neuronal and immune cells.

3. Regulation of Rabies Virus Proteins

Anandamide siRNA was shown to regulate rabies virus proteins. siRNA was directed against the N- and the P-protein of virus strain SAD L16 ( . . . ). By means of virus titration and growth diagrams it was shown that mRNA knockdown negatively affects the whole life cycles of rabies virus.

After infection of the cells with rabies virus and subsequent transfection of different anandamide-siRNA constructs, the virus titer (ffu/mL) was determined in cell medium. A reduction of the virus titer of up to 99% was found.

The experiments were carried out with BJAB cells (Human Burkitt lymphoma B cells), Jurkat cells (human T cell leukemia cells) and E14 cells (cortical mouse neurons).

4. Regulation of Protein FKBP51

In isolated human PBMC cells, anandamide-siRNA conjugates directed against mRNA of protein FKBP51 were tested. FKBP51 regulates signal transduction of steroid hormone receptors and is inter alia associated with certain psychic disorders as well as with Alzheimer.

The experiments showed a protein knockdown of 70%.

REFERENCES (1) Fire, A. Z. Angew. Chem. Int. Ed. 2007, 46, 6966-6984.
(2) Elbashir, S. M.; Harborth, J.; Lendeckel, W.; Yalcin, A.; Weber, K.; Tuschl, T. Nature 2001, 411, 494-498.
(3) Mello, C. C. Angew. Chem. Int. Ed. 2007, 46, 6985-6994.
(4) Bernstein, E.; Caudy, A. A.; Hammond, S. M.; Hannon, G. J. Nature 2001, 409, 363-366.
(5) Castanotto, D.; Rossi, J. J. Nature 2009, 457, 426-433.
(6) Tiemann, K.; Rossi, J. J. EMBO Mol. Med. 2009, 1, 142-151.
(7) Davis, M. E.; Zuckerman, J. E.; Choi, C. H. J.; Seligson, D.; Tolcher, A.; Alabi, C. A.; Yen, Y.; Heidel, J. D.; Ribas, A. Nature 2010, 464, 1067-1070.
(8) Baigude, H.; McCarroll, J.; Yang, C. S.; Swain, P. M.; Rana, T. M. ACS Chem. Biol. 2007, 2, 237-241.
(9) Zimmermann, T. S.; Lee, A. C. H.; Akinc, A.; Bramlage, B.; Bumcrot, D.; Fedoruk, M. N.; Harborth, J.; Heyes, J. A.; Jeffs, L. B.; John, M.; Judge, A. D.; Lam, K.; McClintock, K.; Nechev, L. V.; Palmer, L. R.; Racie, T.; Röhl, I.; Seiffert, S.; Shanmugam, S.; Sood, V.; Soutschek, J.; Toudjarska, I.; Wheat, A. J.; Yaworski, E.; Zedalis, W.; Koteliansky, V.; Manoharan, M.; Vornlocher, H.-P.; MacLachlan, I. Nature 2006, 441, 111-114.
(10) Spagnou, S.; Miller, A. D.; Keller, M. Biochemistry 2004, 43, 13348-13356.
(11) Urban-Klein, B.; Werth, S.; Abuharbeid, S.; Czubayko, F.; Aigner, A. Gene Ther. 2004, 12, 461-466.
(12) Lv, H.; Zhang, S.; Wang, B.; Cui, S.; Yan, J. J. Control. Release 2006, 114, 100-109.
(13) Ma, Z.; Li, J.; He, F.; Wilson, A.; Pitt, B.; Li, S. Biochem. Biophys. Res. Commun. 2005, 330, 755-759.
(14) Akhtar, S.; Benter, I. Adv. Drug Deliv. Rev. 2007, 59, 164-182.
(15) Kurreck, J. Angew. Chem. Int. Ed. 2009, 48, 1378.
(16) Nakagawa, O.; Ming, X.; Huang, L.; Juliano, R. L. J. Am. Chem. Soc. 2010, 132, 8848-8849.
(17) Alam, M. R.; Dixit, V.; Kang, H.; Li, Z. B.; Chen, X.; Trejo, J.; Fisher, M.; Juliano, R. L. Nuc. Acids Res. 2008, 36, 2764-2776.
(18) Alam, M. R.; Ming, X.; Dixit, V.; Fisher, M.; Chen, X.; Juliano, R. L. Oligonucleotides 2010, 20, 103-109.
(19) Ming, X.; Alam, M. R.; Fisher, M.; Yan, Y.; Chen, X.; Juliano, R. L. Nucl. Acids Res. 2010, 38, 6567-6576.
(20) Oishi, M.; Nagasaki, Y.; Itaka, K.; Nishiyama, N.; Kataoka, K. J. Am. Chem. Soc. 2005, 127, 1624-1625.
(21) Leamon, C. P.; Low, P. S. Proc. Natl. Acad. Sci. U.S. A. 1991, 88, 5572-5576.
(22) McNamara, J. O.; Andrechek, E. R.; Wang, Y.; Viles, K. D.; Rempel, R. E.; Gilboa, E.; Sullenger, B. A.; Giangrande, P. H. Nat. Biotech. 2006, 24, 1005-1015.
(23) Lorenz, C.; Hadwiger, P.; John, M.; Vornlocher, H. P.; Unverzagt, C. Bioorg. Med. Chem. Lett. 2004, 14, 4975-4977.
(24) Soutschek, J.; Akinc, A.; Bramlage, B.; Charisse, K.; Constien, R.; Donoghue, M.; Elbashir, S.; Geick, A.; Hadwiger, P.; Harborth, J.; John, M.; Kesavan, V.; Lavine, G.; Pandey, R. K.; Racie, T.; Rajeev, K. G.; Rohl, I.; Toudjarska, I.; Wang, G.; Wuschko, S.; Bumcrot, D.; Koteliansky, V.; Limmer, S.; Manoharan, M.; Vornlocher, H.-P. Nature 2004, 432, 173-178.

(25) Nishina, K.; Unno, T.; Uno, Y.; Kubodera, T.; Kanouchi, T.; Mizusawa, H.; Yokota, T. *Mol. Ther.* 2008, 16, 734-740.
(26) Godfray, J.; Estibeiro, P. *Expert Opin. Ther. Targets* 2003, 7, 363-376.
(27) Wood, M. J. A.; Trülzsch, B.; Abdelgany, A.; Beeson, D. *Hum. Mol. Genet.* 2003, 12, R279-R284.
(28) Filion, M. C.; Phillips, N. C. *Biochim. Biophys. Acta, Biomembr.* 1997, 1329, 345-356.
(29) Pertwee, R. G. *Pharmacol. Ther.* 1997, 74, 129-180.
(30) Devane, W. A.; Hanus, L.; Breuer, A.; Pertwee, R. G.; Stevenson, L. A.; Griffin, G.; Gibson, D.; Mandelbaum, A.; Etinger, A.; Mechoulam, R. *Science* 1992, 258, 1946-1949.
(31) McFarland, M. J.; Porter, A. C.; Rakhshan, F. R.; Rawat, D. S.; Gibbs, R. A.; Barker, E. L. *J. Biol. Chem.* 2004, 279, 41991-41997.
(32) McFarland, M. J.; Barker, E. L. *Pharmacol. Ther.* 2004, 104, 117-135.
(33) Glaser, S. T.; Kaczocha, M.; Deutsch, D. G. *Life Sci.* 2005, 77, 1584-1604.
(34) Burley, G. A.; Gierlich, J.; Mofid, M. R.; Nir, S. T. H.; Eichen, Y.; Carell, T. *J. Am. Chem. Soc.* 2006, 128, 1398.
(35) Gierlich, J.; Burley, G. A.; Gramlich, P. M. E.; Hammond, D. M.; Carell, T. *Org. Lett.* 2006, 8, 3639.
(36) Gramlich, P. M. E.; Warncke, S.; Gierlich, J.; Carell, T. *Angew. Chem. Int. Ed.* 2008, 47, 3442.
(37) El-Sagheer, A. H.; Brown, T. *Proc. Natl. Acad. Sci. U.S.A.* 2010, 107, 15329-15334.
(38) Aigner, M.; Hartl, M.; Fauster, K.; Steger, J.; Bister, K.; Micura, R. *ChemBioChem* 2011, 12, 47-51.
(39) Paredes, E.; Das, S. R. *ChemBioChem* 2011, 12, 125-131.
(40) Xia, W.; Low, P. S. *J. Med. Chem.* 2010, 53, 6811-6824.
(41) Wang, Y.; Juranek, S.; Li, H.; Sheng, G.; Wardle, G. S.; Tuschl, T.; Patel, D. J. *Nature* 2009, 461, 754-761.
(42) Ross, T. L.; Honer, M.; Lam, P. Y. H.; Mindt, T. L.; Groehn, V.; Schibli, R.; Schubiger, P. A.; Ametamey, S. M. *Bioconjugate Chem.* 2008, 19, 2462-2470.
(43) Facci, L.; Daltoso, R.; Romanello, S.; Buriani, A.; Skaper, S. D.; Leon, A. *Proc. Natl. Acad. Sci. U.S.A.* 1995, 92, 3376-3380.
(44) Rakhshan, F.; Day, T. A.; Blakely, R. D.; Barker, E. L. *J. Pharmacol. Exp. Ther.* 2000, 292, 960-967.
(45) Wong, B. R.; Grossbard, E. B.; Payan, D. G.; Masuda, E. S. *Expert Opin. Investig. Drugs* 2004, 13, 743-762.
(46) Ulanova, M.; Duta, F.; Puttagunta, L.; Schreiber, A. D.; Befus, A. D. *Expert Opin. Ther. Targets* 2005, 9, 901-921.
(47) Sanderson, M. P.; Gelling, S. J.; Rippmann, J. F.; Schnapp, A. *Cell. Immunol.* 2010, 262, 28-34.
(48) Martin, B. R.; *J. Pharmacol. Exp. Ther.* 2002, 301, 790-796.
(49) S. Munro, K. L. Thomas, M. Abu-Shaar, *Nature* 1993, 365, 61-65
(50) A. B. Lynn, M. Herkenham, *J. Pharmacol. Exp. Ther.*, 1994, 268, 1612-1623.
(51) L. Facci, R. Dal Toso, S. Romanello, A. Buriani, S. D. Skaper, A. Leon, *Proc. Natl. Acad. Sci. U.S.A.* 1995, 92, 3376-3380.
(52) L. A. Matsuda, S. J. Lolait, M. J. Brownstein, A. C. Young, T. I. Bonner, *Nature* 1990, 346, 561-564.
(53) M. Herkenham, A. B. Lynn, B. R. de Costa, E. K. Richfield, *Brain Res.* 1991, 547, 267-274.
(54) B. F. Thomas, X. Wie, B. R. Martin, *J. Pharmacol. Exp. Ther.* 1992, 263, 1383-1390.
(55) T. M. Westlake, A. C. Howlett, T. I. Bonner, L. A. Matsuda, M. Herkenham, *Neuroscience* 1994, 63, 637-652.

The invention claimed is:

1. A conjugate comprising at least one arachidonic acid residue and covalently bound thereto at least one nucleosidic component selected from nucleic acids, nucleosides and nucleotides.

2. The conjugate of claim 1 having the general formula (Ia) or (Ib)

$$F_n\text{-}(L_m\text{-}N)_r \quad \text{(Ia)}$$

$$F_n\text{-}(L_m\text{-}N)_r\text{-}L_m\text{-}F_n \quad \text{(Ib)}$$

wherein
F is an arachidonic acid residue,
L is a linker,
N is a nucleosidic component selected from nucleic acids, nucleosides and nucleotides,
n is an integer from 1-10,
m is 0 or 1,
r is an integer from 1-25.

3. The conjugate of claim 1 comprising a further ligand covalently bound to the at least one nucleosidic component.

4. The conjugate of claim 3 having the general formula (II)

$$F_n\text{-}(L_m\text{-}N)r\text{-}L_m\text{-}Z_s \quad \text{(II)}$$

wherein
F is an arachidonic acid residue,
L is a linker,
n is an integer from 1-10,
m is 0 or 1,
N is a nucleosidic component selected from nucleic acids, nucleosides and nucleotides,
r is an integer from 1-25,
Z is a further receptor ligand, and
s is an integer from 1-10.

5. The conjugate of claim 1, wherein the arachidonic acid residue is selected from the residue of a free arachidonic acid, an arachidonic acid ester or an arachidonic acid amide, an arachidonic acid sulfonate, an arachidonic acid sulfate, an arachidonic acid phosphonate or an arachidonic acid phosphate.

6. The conjugate of claim 1, wherein the arachidonic acid residue is covalently bound to the at least one nucleosidic component via a linker.

7. The conjugate of claim 6, wherein the linker comprises a cyclic group formed by a Click reaction.

8. The conjugate of claim 1, wherein the nucleosidic component is a nucleic acid molecule.

9. The conjugate of claim 1, wherein the nucleosidic component is a nucleic acid molecule comprising at least one modified building block.

10. The conjugate of claim 1, wherein the nucleosidic component is connected to the arachidonic acid residue via a nucleobase, a sugar or a phosphate group.

11. The conjugate of claim 1, wherein r is an integer from 2-20.

12. The conjugate of claim 1, wherein r is an integer from 2-8.

13. The conjugate of claim 1, wherein n is an integer from 1-5.

14. The conjugate of claim 1, wherein n is 1.

15. The conjugate of claim 6, wherein the linker comprises a 1, 2, 3-triazole group, formed by a Click-reaction between an alkyne and an azide, or a group formed by a Click-reaction between a norbornene and a nitrile imine, a nitrile oxide or a tetrazine.

16. A reagent for manufacturing an RNA-ligand conjugate of the general formula (V):

$$F_n\text{-}(L')_m\text{-}(RG1)_r \qquad (V)$$

wherein
F is an arachidonic acid residue,
n is an integer from 1-10,
m is 0 or 1,
r is an integer from 1-25, L' is a linker, and
RG1 is a Click-reactive group.

17. A reagent for manufacturing a nucleic acid conjugate having the general formula (VI):

$$BB\text{-}(L)_m\text{-}F \qquad (VI)$$

wherein
F is an arachidonic acid residue,
L is a linker,
n is an integer from 1-10,
m is 0 or 1, and
BB is a building block for synthesizing a nucleic acid molecule or a building block suitable for solid phase synthesis.

18. A method of manufacturing a conjugate according to claim 1, comprising
(i) coupling the reagent $$BB\text{-}(L)_m\text{-}F \qquad (VI)$$

with at least one modified RNA molecule (VII)

$$(N)_r\text{-}(L'')_m\text{-}RG2 \qquad (VII)$$

wherein
n is an integer from 1-10,
N is a nucleosidic component selected from nucleic acids, nucleosides and nucleotides,
is an integer from 1-25,
L'' is a linker,
m is 0 or 1, and
RG2 is a Click-reactive group capable of reacting with RG1, thereby forming the conjugate, or
(ii) coupling the reagent $$F_n\text{-}(L')_m\text{-}(RG1)_r \qquad (V)$$

with at least one modified nucleic acid building block (VIII)

$$BB\text{-}(L'')_m\text{-}RG2 \qquad (VIII)$$

wherein
BB is a building block for synthesizing a nucleic acid molecule,
L'' is a linker,
m is 0 or 1, and
RG2 is a Click-reactive group capable of reacting with RG1,
and incorporating the building block having coupled thereto the reagent into a nucleic acid molecule, thereby forming the conjugate.

* * * * *